(12) United States Patent
Kay et al.

(10) Patent No.: US 9,347,073 B2
(45) Date of Patent: May 24, 2016

(54) MINI-INTRONIC PLASMID VECTORS

(71) Applicant: The Board of Trustees of the Leland Stanford Junior University, Palo Alto, CA (US)

(72) Inventors: Mark A. Kay, Los Altos, CA (US); Jiamiao Lu, Mountain View, CA (US)

(73) Assignee: The Board of Trustees of the Leland Stanford Junior university, Stanford, CA (US)

( * ) Notice: Subject to any disclaimer, the term of this patent is extended or adjusted under 35 U.S.C. 154(b) by 0 days.

(21) Appl. No.: 13/744,285

(22) Filed: Jan. 17, 2013

(65) Prior Publication Data

US 2013/0210897 A1 Aug. 15, 2013

Related U.S. Application Data

(60) Provisional application No. 61/597,351, filed on Feb. 10, 2012.

(51) Int. Cl.
| | |
|---|---|
| C12N 15/00 | (2006.01) |
| C12N 15/63 | (2006.01) |
| A61K 48/00 | (2006.01) |
| C12N 15/85 | (2006.01) |
| A01K 67/00 | (2006.01) |

(52) U.S. Cl.
CPC ............ *C12N 15/85* (2013.01); *C12N 2830/42* (2013.01); *C12N 2840/445* (2013.01)

(58) Field of Classification Search
CPC ............... C12N 15/85; C12N 2830/42; C12N 2840/445
USPC ............................... 435/320.1, 455; 424/93.2
See application file for complete search history.

(56) References Cited

U.S. PATENT DOCUMENTS

| | | | |
|---|---|---|---|
| 7,316,925 B2 | 1/2008 | Draghi-Akli et al. | |
| 2010/0008889 A1 | 1/2010 | Mayall et al. | |
| 2010/0303859 A1* | 12/2010 | Williams | 424/215.1 |

FOREIGN PATENT DOCUMENTS

WO  03/104412  12/2003

OTHER PUBLICATIONS

Lavigueur et al. A splicing enhancer in the human fibronectin alternate ED1 exon interacts with SR proteins and stimulates U2 snRNP binding. Genes & Development 7:2405-2417, 1993.*
Lu et al. The extragenic spacer length between the 5' and 3' ends of the transgene expression cassette affects transgene silencing from plasmid-based vectors. Molecular Therapy 20:2111-2119, 2012.*
Muhlbauer et al. Functional analysis of plastid DNA replication origins in tobaccor by targeted inactivation. Plant J. 32:175-184, 2002.*
Galmozzi; et al., "Exon 3 of the alpha folate receptor gene contains a 5' splice site which confers enhanced ovarian carcinoma specific expression", FEBS Lett. (Jul. 2001), 502(1-2):31-4.

* cited by examiner

*Primary Examiner* — Quang Nguyen
(74) *Attorney, Agent, or Firm* — Kyle A. Gurley; Bozicevic, Field & Francis LLP

(57) ABSTRACT

Compositions and methods are provided for achieving persistent, high level expression of transgenes in vitro and in vivo. Aspects of the invention include vectors comprising an intronic cassette that comprises plasmid elements, and methods that rely on the use of vectors comprising an intronic cassette that comprises plasmid elements. These compositions and methods find use in many applications, including therapeutic applications such as in gene therapy; synthesis applications such as in the synthesis of peptides, proteins, and RNAs, e.g. for research or therapeutic purposes; and research applications, such as in the production of transgenic cells and animals. In addition, reagents, devices and kits thereof that find use in making the subject compositions and practicing the subject methods are provided.

30 Claims, 33 Drawing Sheets
(3 of 33 Drawing Sheet(s) Filed in Color)

| DNA vector | size (kb) | vector yield (mg/l) | vector yield (E-9 mole/l) |
|---|---|---|---|
| MIP.5'OIPR.RHB | 3.5 | 8.11 ± 0.76 | 3.49 ± 0.65 |
| pMIP.RHB | 3.3 | 7.01 ± 0.51 | 3.27 ± 0.24 |
| pRHB | 5.0 | 3.12 ± 0.52 | 0.95 ± 0.16 |
| TOPO2.1 Empty Vector | 3.9 | 3.17 ± 0.39 | 1.23 ± 0.15 |

(b)

Optimized Intron 2 (Ointron2)

5' attggg*ATCTTC*acacagcag—intron2—gccgcaag*CTGAAG*cgtgtcc3'

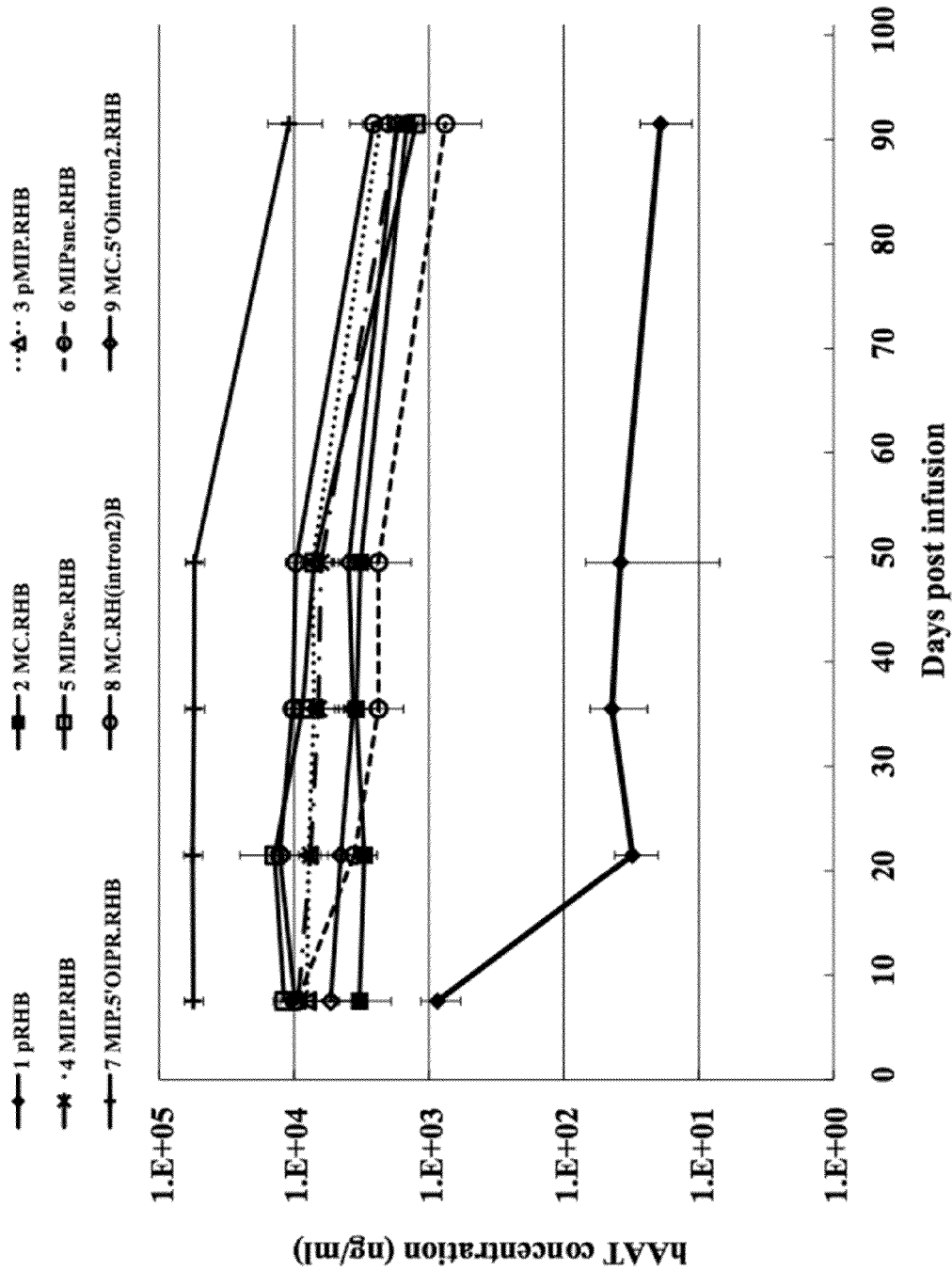

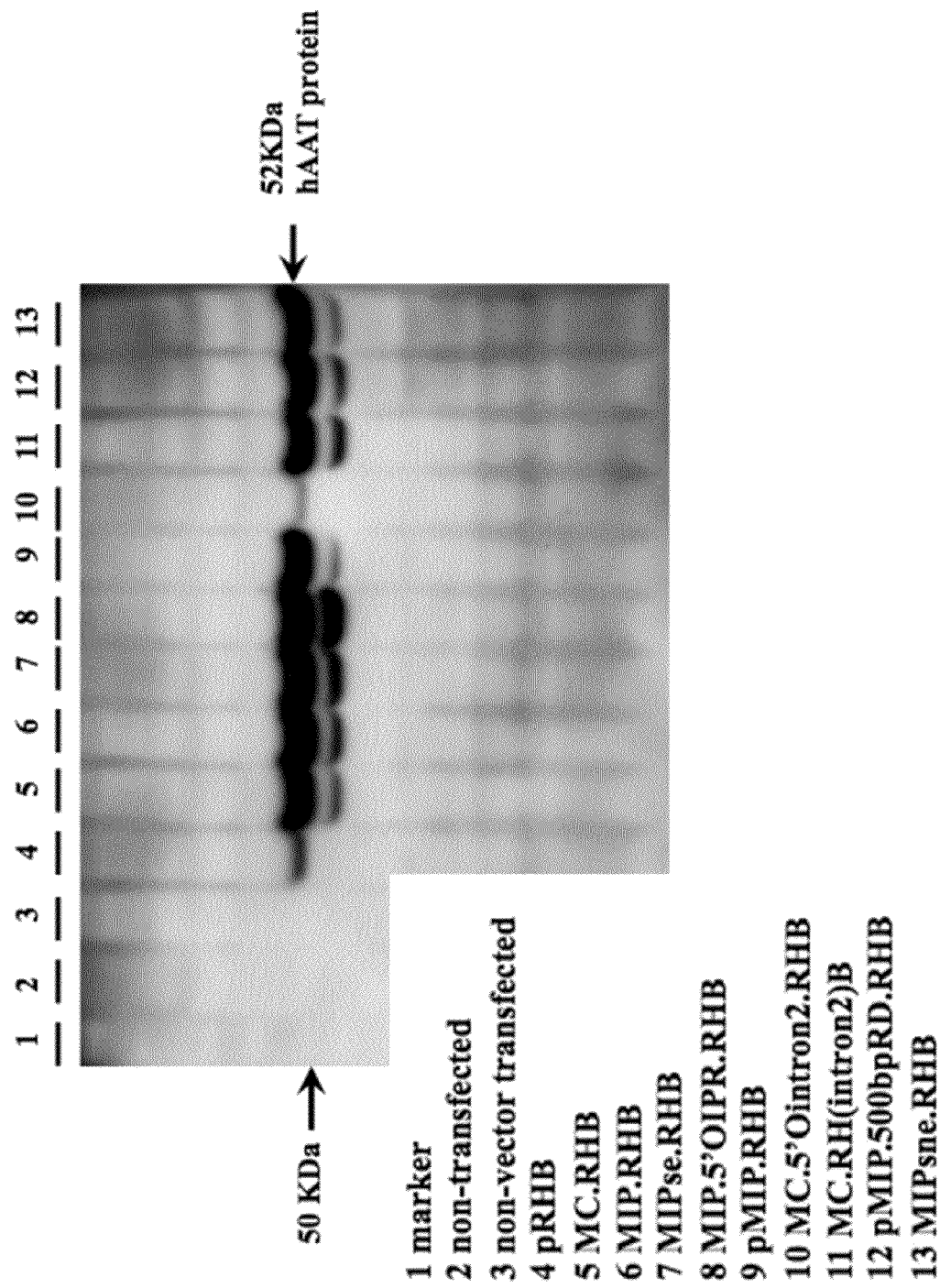

1 pApoE.hFIX.hGHpA

2 MC.ApoE.hFIX.hGHpA

3 MIP.ApoE.hFIX.hGHpA 1 pRSV.Luc2.bpA

2 MC.RSV.Luc2.bpA

3 MIP.RSV.Luc2.bpA 1  pRHB+ pRSV.GFP

2  MC.RHB+ pRSV.GFP

3  MIP.5'OIPR.RHB + pRSV.GFP 4  pMIP.RHB + pRSV.GFP

FIGURE 7A

```
        10         20         30         40         50         60         70         80         90        100
  1 gccgcctac taagcaget ttttttctt aCCccttctt cgctccte gctcactgac tgctgcgct cggtcgttcg actgcggcga gcggtatcag  100
101 ctcactcaaa ggcggtaata cggttatcca cagaatcagg ggataacgca ggaaagaaca tgtgagcaaa aggccagcaa aaggccagga accgtaaaaa  200
201 ggccgcgttg cgtttcccc tcaagagcet cgccgcccct gacgagcatc acaaaaatcg acgctcaagt cagaggtggc gaaacccgac aggactataa  300
301 agataccagg cgtttccccc ctggaagetc cctcgtgcgc tctcctgttc cgaccctgcc gcttaccgga tacctgtccg cctttctccc ttcgggaageg  400
401 tggcgcttc tcatagctca cgctgtaggt atctcagttc ggtgtaggtc gttcgctcca agctgggctg tgtgcacgaa ccccccgttc agcccgaccg  500
501 ctgcgcctta tccggtaact atcgtcttga gtccaacccg gtaagacacg acttatcgcc actggcagca gccactggta acaggattag cagagcgagg  600
601 tatgtaggcg gtgctacaga gttcttgaag tggtggccta actacggcta cactagaaga acagtatttg gtatctgcgc tctgctgaag ccagttacct  700
701 tcggaaaaag agttggtagc tcttgatccg gcaaacaaac caccgctggt agcggtggtt tttttgtttg caagcagcag attacgcgca gaaaaaaagg  800
801 atctcaagaa gatcctttga tcttttctac ggggtctgac gctcagtgga acgaaaactc acgttaaggg attttggtca tgagattatc aaaaaggatc  900
901 ttcacctaga tccttttaaa ttaaaaatga agttttaaat caatctaaag tatatatgag taaacttggt ctgacagtta ccaatgctta atcagtgagg 1000
1001 cacctatctc agcgatctgt ctatttcgtt catccatagt tgcctgactc cccgtcgtgt agataactac gatacgggag GGCTTACCAT CTGGCCCCAG 1100
1101 GAGTCGCAC ATCTTGTTGT CTGATTATTG ATTTTTGGCG AAACCATTTG AAACCATTTG AAACCATTTG ATCATATGAC AGATGTGTA TCTACCTTAA GAGAGTCGT GTAAAATATC TTGATAAAAA 1200
1201 TCATTAGGTA ccccggc                                                                                           1217
        10         20         30         40         50         60         70         80         90        100
```

FIGURE 7B 1 pRHB

2 MC.RHB

3 MIP.5'OIPKan.RHB

AAV8.MIP.5'OIPR.RHB

AAV8.RHB

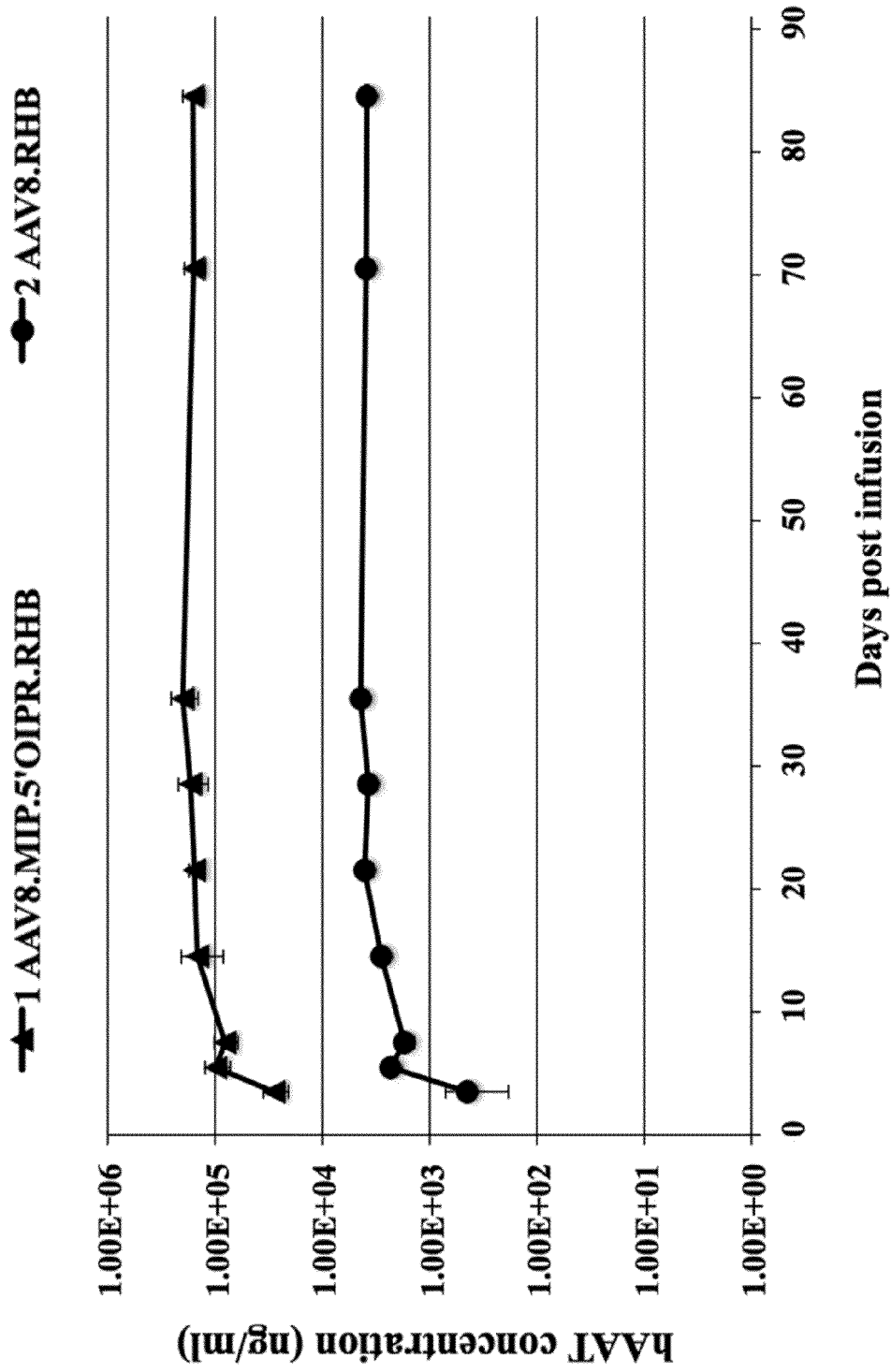

SEQUENCE LISTING

<160> NUMBER OF SEQ ID NOS: 33

<210> SEQ ID NO 1
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 1
attgggatct tcacacagca ggtaaggttg cgggccgggc ctgggccggg tccgggccgg        60
g                                                                      61

<210> SEQ ID NO 2
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 2
ccgcactgac ccctggtgtt gctttttttt tttaggccgc aagctgaagc gtgtcc           56

<210> SEQ ID NO 3
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 3
attgggatct tcacacagca g                                                 21

<210> SEQ ID NO 4
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 4
gccgcaagct gaagcgtgtc c                                                 21

<210> SEQ ID NO 5
<211> LENGTH: 1217
<212> TYPE: DNA
<213> ORGANISM: Artificial Sequence
<220> FEATURE:
<223> OTHER INFORMATION: synthetic oligonucleotide

<400> SEQUENCE: 5
gcccgcctaa tgagcgggct ttttttcctt accccttctt ccgcttcctc gctcactgac        60
tcgctgcgct cggtcgttcg gctgcggcga gcggtatcag ctcactcaaa ggcggtaata       120
cggttatcca cagaatcagg ggataacgca ggaaagaaca tgtgagcaaa aggccagcaa       180
aaggccagga accgtaaaaa ggccgcgttg ctggcgtttt tccataggct ccgcccccct       240

```
gacgagcatc acaaaaatcg acgctcaagt cagaggtggc gaaacccgac aggactataa      300
agataccagg cgtttccccc tggaagctcc ctcgtgcgct ctcctgttcc gaccctgccg      360
cttaccggat acctgtccgc ctttctccct tcgggaagcg tggcgctttc tcatagctca      420
cgctgtaggt atctcagttc ggtgtaggtc gttcgctcca agctgggctg tgtgcacgaa      480
ccccccgttc agcccgaccg ctgcgcctta tccggtaact atcgtcttga gtccaacccg      540
gtaagacacg acttatcgcc actggcagca gccactggta acaggattag cagagcgagg      600
tatgtaggcg gtgctacaga gttcttgaag tggtggccta actacggcta cactagaaga      660
acagtatttg gtatctgcgc tctgctgaag ccagttacct tcggaaaaag agttggtagc      720
tcttgatccg gcaaacaaac caccgctggt agcggtggtt ttttgtttg caagcagcag      780 attacgcgca gaaaaaaagg atctcaagaa gatcctttga tcttttctac ggggtctgac      840
gctcagtgga acgaaaactc acgttaaggg attttggtca tgagattatc aaaaaggatc      900
ttcacctaga tccttttaaa ttaaaaatga agttttaaat caatctaaag tatatatgag      960
taaacttggt ctgacagtta ccaatgctta atcagtgagg cacctatctc agcgatctgt     1020
ctatttcgtt catccatagt tgcctgactc ctgcaaacca cgttgtggta gaattggtaa     1080
agagagtcgt gtaaaatatc gagttcgcac atcttgttgt ctgattattg attttggcg     1140 aaaccatttg atcatatgac aagatgtgta tctaccttaa cttaatgatt ttgataaaaa     1200
tcattaggta ccccggc                                                   1217

<210> SEQ ID NO 6
<211> LENGTH: 1338
<212> TYPE: DNA
<213> ORGANISM: Artificial Sequence
<220> FEATURE:
<223> OTHER INFORMATION: synthetic oligonucleotide

<400> SEQUENCE: 6
attgggatct tcacacagca ggtaaggttg cgggccgggc ctgggccggg tccgggccgg       60
gtattgcccg cctaatgagc gggcttttt ttcttacccc ttcttccgct tcctcgctca      120
ctgactcgct gcgctcggtc gttcggctgc ggcgagcggg atcagctcac tcaaaggcgg      180
taatacggtt atccacagaa tcaggggata acgcaggaaa gaacatgtga gcaaaaggcc      240
agcaaaaggc caggaaccgt aaaaaggccg cgttgctggc gttttccat aggctccgcc      300 cccctgacga gcatcacaaa aatcgacgct caagtcagag gtggcgaaac ccgacaggac      360
tataaagata ccaggcgttt ccccctggaa gctccctcgt gcgctctcct gttccgaccc      420
tgccgcttac cggatacctg tccgcctttc tcccttcggg aagcgtggcg ctttctcata      480
gctcacgctg taggtatctc agttcggtgt aggtcgttcg ctccaagctg ggctgtgtgc      540
acgaaccccc cgttcagccc gaccgctgcg ccttatccgg taactatcgt cttgagtcca      600
acccggtaag acacgactta tcgccactgg cagcagccac tggtaacagg attagcagag      660
cgaggtatgt aggcggtgct acagagttct tgaagtggtg gcctaactac ggctacacta      720
gaagaacagt atttggtatc tgcgctctgc tgaagccagt taccttcgga aaaagagttg      780
gtagctcttg atccggcaaa caaaccaccg ctggtagcgg tggttttttt gtttgcaagc      840
agcagattac gcgcagaaaa aaaggatctc aagaagatcc tttgatcttt tctacggggt      900
ctgacgctca gtggaacgaa aactcacgtt aagggatttt ggtcatgaga ttatcaaaaa      960
ggatcttcac ctagatcctt ttaaattaaa aatgaagttt taaatcaatc taaagtatat     1020
```

-continued

```
atgagtaaac ttggtctgac agttaccaat gcttaatcag tgaggcacct atctcagcga      1080
tctgtctatt tcgttcatcc atagttgcct gactcctgca aaccacgttg tggtagaatt      1140
ggtaaagaga gtcgtgtaaa atatcgagtt cgcacatctt gttgtctgat tattgatttt      1200
tggcgaaacc atttgatcat atgacaagat gtgtatctac cttaacttaa tgattttgat      1260
aaaaatcatt aggtaccccg gcccgcactg acccctggtg ttgcttttt tttttaggcc       1320 gcaagctgaa gcgtgtcc                                                    1338
```

```
<210> SEQ ID NO 7
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 7
gggccgggcc tgggccgggt ccgggccggg                                         30
```

```
<210> SEQ ID NO 8
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 8
gcccgcctaa tgagcgggc                                                     19
```

```
<210> SEQ ID NO 9
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 9
ggccggggta cctaatgatt t                                                  21
```

```
<210> SEQ ID NO 10
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 10
ttcccctctc tccaggtctg ccagcttaca tttacc                                  36
```

```
<210> SEQ ID NO 11
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 11
gttgagcaac cttaccttct gtcttcattt tccagg                                  36
```

```
<210> SEQ ID NO 12
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 12
gtaaggttgc tcaaccagcc                                              20

<210> SEQ ID NO 13
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 13
ctggagagag gggaaggtg                                               19

<210> SEQ ID NO 14
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 14
agcaggtaag gttgctcaac cagcc                                        25

<210> SEQ ID NO 15
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 15
ttcagcttgc ggcctggaga gagggaagg tg                                 32

<210> SEQ ID NO 16
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 16
aggccgcaag ctgaagcgt                                               19

<210> SEQ ID NO 17
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 17
gcaaccttac ctgctgtgtg                                              20

<210> SEQ ID NO 18
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 18
acgcgtccaa ttgcctttct                                              20

<210> SEQ ID NO 19
```

<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 19
ctcgaggttg aaggtctcaa                                                    20

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 20
aaggcaaatg ggagagacct                                                    20

<210> SEQ ID NO 21
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 21
tacccagctg gacagcttct                                                    20

<210> SEQ ID NO 22
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 22
ttgctgacag gatgcagaag                                                    20

<210> SEQ ID NO 23
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 23
tgatccacat ctgctggaag                                                    20

<210> SEQ ID NO 24
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 24
gccgtcttct gtctcgtgg                                                     19

<210> SEQ ID NO 25
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 25
aagaagatat tggtgctgtt gg                                                  22

<210> SEQ ID NO 26
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 26
gtagaattgg taaagagagt cg                                                  22

<210> SEQ ID NO 27
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 27
ggtacctaat gattttatc aaaa                                                 24

<210> SEQ ID NO 28
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 28
ttatttttgg gtgggattca cc                                                  22

<210> SEQ ID NO 29
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 29
ggtaaagaga gtcgtgtaaa at                                                  22

<210> SEQ ID NO 30
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 30 gattttatc aaaatcatta agttaa                                               26

<210> SEQ ID NO 31
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 31
aaggcaaatg ggagagacct                                                     20

<210> SEQ ID NO 32
<211> LENGTH: 19
<212> TYPE: DNA

```
<213> ORGANISM: Artificial Sequence
<220> FEATURE:
<223> OTHER INFORMATION: synthetic oligonucleotide

<400> SEQUENCE: 32
acccagctgg acagcttct                                               19

<210> SEQ ID NO 33
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 33
atgggatctt cacacagcag gccgcaagct gaagcgtgtc c                      41
```

US 9,347,073 B2

MINI-INTRONIC PLASMID VECTORS

CROSS REFERENCE TO RELATED APPLICATIONS

Pursuant to 35 U.S.C. §119 (e), this application claims priority to the filing date of the U.S. Provisional Patent Application Ser. No. 61/597,351 filed Feb. 10, 2012; the disclosure of which are herein incorporated by reference.

GOVERNMENT RIGHTS

This invention was made with government support under HL064274 awarded by the National Institutes of Health. The Government has certain rights in the invention.

FIELD OF THE INVENTION

This invention pertains to the use of mini-intronic plasmid vectors for the long-term expression of transgenes.

BACKGROUND OF THE INVENTION

The introduction of an exogenous nucleic acid sequence (e.g., DNA) into a cell, a process known as "transformation," plays a major role in a variety of biotechnology and related applications, including research, synthetic and therapeutic applications. Research applications in which transformation plays a critical role include the production of transgenic cells and animals. Synthetic applications in which transformation plays a critical role include the production of peptides and proteins, as well as therapeutic RNAs, such as interference RNA or ribozymes. Therapeutic applications in which transformation plays a key role include gene therapy applications.

In many of these applications, it is desirable to introduce the exogenous DNA in a manner such that it provides for long-term expression of the protein or RNA encoded by the exogenous DNA. Long-term expression is primarily achieved through one of two routes: integration of the exogenous DNA into a target cell's genome, or extrachromosomal expression of the exogenous DNA from minicircle vectors. Extrachromosomal expression from minicircles avoids the pitfalls associated with integration, including the accidental interruption of important genes, and the aberrant expression or silencing of the integrated DNA due to the activity at the locus of integration, etc. However, the production of minicircle vectors is a multistep, time-consuming process. What is required is a composition that provides the advantages of minicircle vectors with the ease of preparation of a plasmid.

The present invention addresses these issues.

SUMMARY OF THE INVENTION

Compositions and methods are provided for achieving persistent, high level expression of transgenes in vitro and in vivo. Aspects of the invention include vectors comprising an intronic cassette that comprises plasmid elements, and methods that rely on the use of vectors comprising an intronic cassette that comprises plasmid elements. These compositions and methods find use in many applications, including therapeutic applications such as in gene therapy; synthesis applications such as in the synthesis of peptides, proteins, and RNAs, e.g. for research or therapeutic purposes; and research applications, such as in the production of transgenic cells and animals. In addition, reagents, devices and kits thereof that find use in making the subject compositions and practicing the subject methods are provided.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 7: Detailed sequence for PR and OIPR fragments. A) PR sequence (SEQ ID NO:5). The PR sequence was isolated from NTC8385-EGFP vector (Nature Technology Corporation). Capitalized sequence "CC" (32-33) was mutated from original sequence "gg" to prevent formation of a potential alternative splice site. The trpA prokaryotic terminator (underlined sequence 1-30) in this PR sequence prevents prokaryotic transcription during selection. The RNA-OUT selectable marker (capitalized sequence 1066-1210) expresses a 145 bp RNA-OUT antisense RNA, which represses the expression of a counter-selectable marker, SacB from the host bacteria. SacB gene encodes levansucrase, which is toxic to bacteria in the presence of sucrose. Thus vectors with the RNA-OUT selectable marker enable the host bacteria to grow on media in the presence of sucrose (Luke et al., Improved antibiotic-free DNA vaccine vectors utilizing a novel RNA based plasmid selection system. *Vaccine* 27, 6454-6459, (2009)). B) OIPR sequence (SEQ ID NO:6). 5'ESE is indicated as capitalized sequence 7-12. G triplets are capitalized sequence 32-65. BPS is capitalized sequence 1288-1292. 11 nucleotides polypyrimidine sequence is capitalized from 1305-1315. 3'ESE is indicated as capitalized sequence 1326-1331.

Figure 1A:
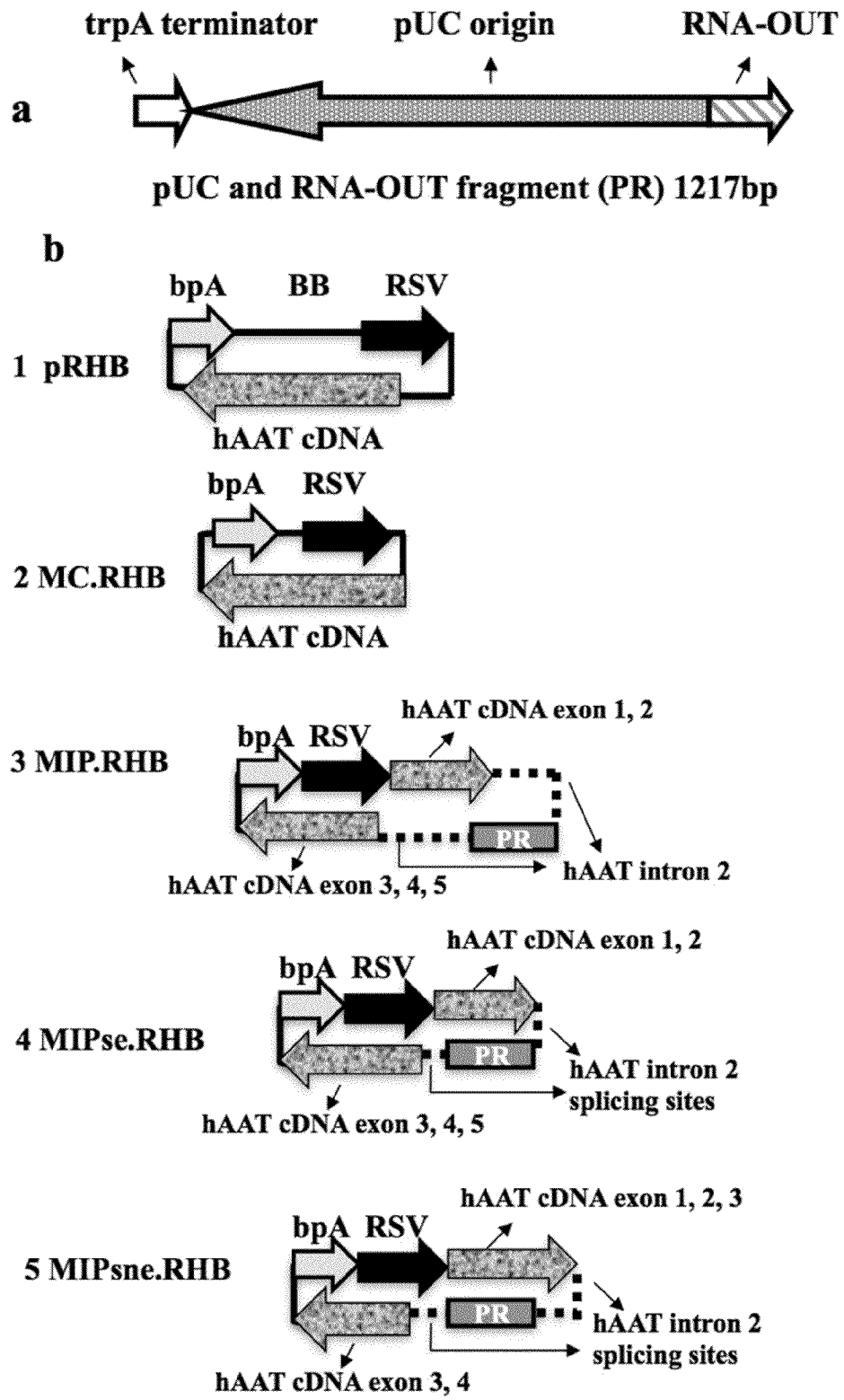
FIG. 1: RSV-hAAT expression constructs and transgene expression in mice. A) DNA constructs. A(a) Schematic structure of the PR sequence. A(b) Schematic of DNA constructs containing the PR sequence in the intron region. B) Serum hAAT levels at various time points (3 days, 1 week, 3 weeks, 5 weeks, and 18 weeks) after equimolar infusion of one of the vectors were infused. (n=5/group, one animal from each group was terminated on day 35). Error bars represent the standard deviation. C) Copy number of each construct per diploid genome in liver sample 35 days after infusion was determined by quantitative real time PCR. The mean value was determined by isolating duplicate samples from each animal and was indicated on each bar. For pRHB, 2.0 (2.2, 1.8). MC.RHB, 1.8 (1.8, 1.8). For MIP.RHB, 2 (2.1, 1.9). For MIP.seRHB, 2.0.(2.3, 1.7). For MIPsne.RHB, 2.5 (2.5, 2.5). D) Northern blot data. One 35 day post-infusion liver total RNA sample was extracted from each treated group and probed for hAAT and β-actin transcripts.

RSV-hAAT expression cassettes that are inserted into NdeI and NheI sites of p388-AC-For in A to produce final AAV8 recombinant vector genome. B1) RSV-hAAT expression cassette that contains OIPR sequence in the 5' non-coding exon was used to produce AAV8.MIP.5'OIPR.RHB recombinant vector genome. B2) RSV-hAAT expression cassette was used to produce conventional AAV8.RHB recombinant vector genome. C) Same titer amount of AAV8 shown in B were infused into C57BL/6 mice (n=5/group) and the serum hAAT determined at various time points (3 days, 5 days, 1 week, 2 weeks, 3 weeks, 4 weeks, 5 weeks, 10 weeks and 12 weeks) through ELISA. Error bars represent the standard deviation.

DETAILED DESCRIPTION OF THE INVENTION

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

By a "DNA molecule" it is meant the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

By an "expression cassette" it is meant a polynucleotide comprising a DNA coding sequence operably linked to a promoter.

By a DNA "coding sequence" it is meant a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

"DNA regulatory sequences", as used herein, are transcriptional and translational control sequences, such as promoters, enhancers, polyadenylation signals, terminators, and the like, that provide for and/or regulate expression of a coding sequence in a host cell.

As used herein, a "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters may be used to drive the various vectors of the present invention. For example, the promoter may be a constitutively active promoter, i.e. a promoter that is active in the absence externally applied agents, e.g. the CMV IE1 promoter, the SV40 promoter, the GAPDH promoter, the RSV promoter, the Actin promoter, and the like. The promoter may be an inducible promoter, i.e. a promoter whose activity is regulated upon the application of an agent to the cell, e.g. doxycycline, the tet-on or tet-off promoter, the estrogen receptor promoter, etc. The promoter may be a tissue-specific promoter, i.e. a promoter that is active in certain types of cells.

As used herein, the term "transgene" refers to a polynucleotide sequence that encodes a product and is capable of being expressed in a target cell. Non-limiting examples of transgenes include polynucleotide sequences that encode a peptide or polypeptide, and polynucleotide sequences that encode a non-translated ribonucleic acid, e.g. a double stranded RNA or a single stranded RNA, e.g. antisense RNA, siRNA, shRNA, miRNA, etc.

As used herein, the term "reporter gene" refers to a coding sequence attached to heterologous promoter or enhancer elements and whose product may be assayed easily and quantifiably when the construct is introduced into tissues or cells.

By an "intron" it is meant a polynucleotide sequence that, when transcribed, e.g. as part of a gene, is biochemically removed ("spliced") from the transcript by the splicesome prior to translation of the transcript.

By an "intronic cassette" it is meant a polynucleotide sequence comprising an intron as well as one or more other elements, e.g. splice donor sequence, splice acceptor sequence, G triplet sequence, pyrimidine-rich tract, consensus branch point sequence, etc. that promote out-splicing of the intron.

By a "vector" it is meant a nucleic acid that is capable of transferring a polynucleotide sequence, e.g. a transgene, to a target cell. For the purposes of the present invention, "vector construct," "expression vector," and "gene transfer vector," generally refer to any nucleic acid construct, for example, a linear nucleic acid, a circular nucleic acid, a phage, a virus, a cosmid, and the like, that is capable of transferring a gene of interest into target cells. Thus, the term includes cloning and expression vehicles, and extrachromosomally maintained vectors as well as integrating vectors.

By a "plasmid" it is meant a circular vector that comprises an origin of replication and a selectable marker.

By a "plasmid backbone" it is meant the region of a plasmid that comprises the origin of replication and selectable marker, as well as bacterial sequences that flank these elements.

By an "origin of replication" or "replication origin" it is meant a particular sequence in a genome at which replication is initiated. Origins of replication are found in prokaryotes and eukaryotes, and are required for the propagation of the plasmid episomally (i.e. extragenomically) in host cells.

By a selectable, or "selection", marker, it is meant a coding sequence that allows for selective retention of cells comprising a nucleic acid of interest, e.g. a plasmid, during culturing and propagation in the host cells. Non-limiting examples of selectable markers include those genes useful in antibiotic resistance systems, e.g. amp, kana, neo; those useful in balanced lethal systems, in which an essential gene is maintained on the plasmid with a corresponding chromosomal deletion or suppressible mutation on the host cell genome, e.g. a tRNA selectable marker that suppresses a host chromosomal arg gene mutation; those useful in repressor titration systems, in which an operator sequences, e.g. the lac operator or tet operator, placed on a multicopy plasmid, derepresses a chromosomal gene; antidote/poison selection schemes, in which an antidote (e.g. the ccdA gene) to a poison expressed from the host chromosome (e.g. the ccdB gene) is maintained on the plasmid; and those useful in RNA-based selection schemes, e.g. RNAI and RNAII antisense regulators, or antisense regulators (e.g. RNA-OUT, e.g. the PR sequence described in the working examples below and in FIG. 7A) that inhibit the translation of a gene (SacB) transcribed from the host chromosome that would otherwise promote cell death.

By a "minicircle vector" it is meant a small, double stranded circular DNA molecule that provides for persistent, high level expression of a sequence of interest that is present on the vector. The sequence of interest is operably linked to regulatory sequences present on the minicircle vector, which regulatory sequences control its expression. Such minicircle vectors are described, for example in published U.S. Patent Applications US20040214329 and US 20110244566 herein specifically incorporated by reference. Minicircle vectors differ from bacterial plasmids in that they lack an origin of replication, and lack selectable markers commonly found in bacterial plasmids, e.g. β-lactamase, tet, and the like. Consequently, minicircles are small in size, allowing more efficient delivery to a cell. More importantly, minicircles are devoid of the transgene expression silencing effect which is associated with these plasmid backbone nucleic acid sequences.

As used herein, a cell has been "transformed" or "transfected" by exogenous or heterologous DNA, e.g. a DNA construct, when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). In keeping with standard polypeptide nomenclature, NH2 refers to the free amino group present at the amino terminus (the N terminus) of a polypeptide, while COON refers to the free carboxy group present at the carboxy terminus (the C terminus) of a polypeptide.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Compositions and methods are provided for achieving persistent, high level expression of transgenes in vitro and in vivo. Aspects of the invention include vectors comprising an intron that comprises plasmid elements, and methods that rely on the use of vectors comprising an intron that comprises plasmid elements. These compositions and methods find use in many applications, including therapeutic applications such as in gene therapy; synthesis applications such as in the synthesis of peptides, proteins, and RNAs, e.g. for research or therapeutic purposes; and research applications, such as in the production of transgenic cells and animals. In addition, reagents, devices and kits thereof that find use in making the subject compositions and practicing the subject methods are provided. These and other objects, advantages, and features of the invention will become apparent to those persons skilled Compositions In some aspects of the invention, a mini-intronic plasmid vector is provided. By a mini-intronic plasmid vector, or "MIP vector", or simply "MIP", it is meant a vector that provides for the persistent, high level expression of a transgene of interest in mammalian cells while comprising an origin of replication and/or a selectable marker. By a vector it is meant a nucleic acid, e.g., a linear nucleic acid, a circular nucleic acid, a phage, a virus, a cosmid, and the like, that is that is capable of transferring a polynucleotide sequence to target cells. By a transgene, it is meant any polynucleotide sequence that encodes a peptide/polypeptide or a non-translated ribonucleic acid, e.g. a double stranded RNA or a single stranded RNA, e.g. antisense RNA, siRNA, shRNA, miRNA. By high level expression, it is meant that the transgene is expressed by a host cell at a level that is 50-fold greater, 100-fold (2-log) greater, 1000-fold (3-log) greater, or 10,000 fold (4-log) greater or more, within the first 1, 2, or 3 days following transformation than in the absence of vector. By persistent, it is meant that high level expression of the transgene persists for 2 weeks or more, for example, 3 weeks or more, 5 weeks or more, 7 weeks or more, 9 weeks or more, 13 weeks or more, 18 weeks or more, 6 months or more, e.g. 12 months. In other words, the expression level of the transgene does not decrease more than 100-fold, more usually not more than 50-fold, in some instances, not more than 10-fold in the 2 weeks or more, i.e. 3 weeks, 5 weeks, 7 weeks, 9 weeks or more, 13 weeks or more, 18 weeks or more, 6 months or more following transformation from levels observed within the first 1, 2, or 3 days.

Bacterial elements useful for the propagation of a plasmid, i.e. origin of replication, and selection of the plasmid in bacteria, i.e. selectable markers, have been shown previously to promote silencing of transgenes that are expressed from a vector, e.g. as a plasmid. However, the inventors of the subject application have made the surprising discovery that origins of replication and selectable markers do not have a silencing effect on transgene expression if they are included in the vector as part of an intron within an expression cassette, e.g. within the transgene. In other words, the inventors have discovered that a vector comprising an intron comprising a bacterial origin of replication and a selectable marker—and substantially free of such plasmid backbone sequences anywhere else on the plasmid (that is, external to the intron)—will provide for persistent, high level expression of a transgene expressed from the expression cassette, e.g. expression that is 5-fold greater or more, e.g, 10-fold greater more, 50-fold greater or more, in some instances 100-fold greater, than a vector comprising an origin of replication and selectable marker that are not in an intron, i.e. a plasmid. This arrangement provides the benefit of providing for persistent, high level expression of a nucleic acid of interest from the vector (as compared to a plasmid comprising a plasmid backbone, which does not), while also allowing the vector to be propagated and selected for in bacteria (as compared to a minicircle vector, which cannot).

As such, in aspects of the invention, a MIP vector is provided, wherein the MIP vector comprises an intron comprising an origin of replication and/or a selectable marker. In some instances, the intron of the MIP vector may be part of an intronic cassette. By an "intronic cassette" it is meant a polynucleotide sequence comprising an intron (comprising the bacterial origin of replication and selectable marker) as well as other elements that promote out-splicing of the intron. For example, the intronic cassette may comprise a splice donor sequence and a splice acceptor sequence. Splice donor and splice acceptor sequences are the nucleotide sequences that flank the intron and guide the splicing, i.e. biochemical processing, of pre-mRNA transcripts by the splicesome, at which time introns are removed and exons are joined to form mature mRNA transcripts. The splice donor sequence, also known as a 5' splice site, is the sequence that flanks the 5' end of an intron, and typically comprises an AG dinucleotide. The splice acceptor sequence, also known as a 3' splice site, is the sequence that flanks the 3' end of the intron, and typically comprises a GC dinucleotide. Any splice donor sequence and splice acceptor sequence may be used in the intronic cassette of a MIP. For example, the splice donor and acceptor sequences may be the splice donor and acceptor sequences that flank an intron normally found in nature. Alternatively, the splice donor and acceptor sequences may be optimized splice donor and acceptor sequences, e.g. they may comprise a 5' exonic splicing enhancer (ESE) and/or a 3' exonic splicing enhancer (ESE) (Fairbrother W G, et al. Predictive identification of exonic splicing enhancers in human genes. *Science* 297: 1007-1013, (2002)) such as ATCTTC and CTGAAG, respectively, e.g. as depicted in nucleotides 7-12 and 26-31, respectively, of FIG. 7B. As another example, the intronic cassette may comprise a G triplet sequence, e.g. gggccgggC-CTgggccgggTCCgggccggg (SEQ ID NO:7) (McCullough A J, Berget S M (1997) "G triplets located throughout a class of small vertebrate introns enforce intron borders and regulate splice site selection". Mol Cell Biol 17: 4562-4571), e.g. as depicted in nucleotides 32-65 of FIG. 7B. The intronic cassette may comprise a sequence, or "tract", that is rich in pyrimidines e.g. a tract of 5-20 pyrimidines, e.g. 8-15 pyrimidines, e.g. 10-13 pyrimidines (Coolidge C J, et al. (1997). "Functional analysis of the polypyrimidine tract in pre-mRNA splicing". Nucleic Acids Res 25: 888-896). The intronic cassette may comprise a consensus branch point sequence (BPS), e.g. yUnAy (y being any pyrimidine, n being any nucleotide) encoded by yTnAy, e.g. CTGAC. (Gao et al. (2008) "Human branch point consensus sequence is yUnAy." Nucleic Acids Res. 36(7):2257-2267). Thus, the intronic cassette may comprise a number of sequences that are exogenous to the transgene.

In some embodiments, the subject vectors comprise one or more expression cassettes. By an "expression cassette" it is meant any nucleic acid construct capable of directing the expression of any RNA transcript including gene/coding sequence, i.e. a transgene, of interest. Expression cassettes comprise a promoter that is recognized by the host organism and is operably linked to the coding sequence, i.e. transgene. By a promoter it is meant an untranslated sequences located upstream (5') to the start codon of a structural gene (generally within about 100 to 1000 bp) that modulates the transcription and translation of particular nucleic acid sequence to which they are operably linked. By modulating transcriptional activation, it is meant that transcription will be modulated, e.g. increased, from basal levels in the target cell by at least about 10 fold, by at least about 100 fold, more usually by at least about 1000 fold. Such promoters typically fall into two classes, inducible and constitutive. Inducible promoters are promoters that initiate increased levels of transcription from DNA under their control in response to some change in culture conditions, e.g., the presence or absence of a nutrient, drug, change in temperature, or change in expression of a protein in a cell, e.g. the tetracycline-inducible promoters. Constitutive, or ubiquitously acting, promoters are always active, e.g. the CMV-β-actin promoter/enhancer. A large number of promoters recognized by a variety of potential host cells are well known. Both a native promoter sequence and many heterologous promoters may be used to direct expression of transgene of interest. However, heterologous promoters are preferred, as they generally permit greater transcription and higher yields.

Transcription by higher eukaryotes of transgenes in expression cassettes may be increased by inserting an enhancer sequence into the vector. Enhancers are cis-acting elements of DNA, usually about from 10 to 300 bp, which act on a promoter to increase its transcription. Enhancers are relatively orientation- and position-independent, having been found 5' and 3' to the transcription unit, within an intron, as well as within the coding sequence itself.

Expression cassettes may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the transgene of interest.

In some instances, the intronic cassette of the subject vectors is operably linked to the same promoter that will mediate the expression of the transgene of interest from the MIP vector. In other words, the expression cassette that comprises the transgene of interest also comprises the intronic cassette. In such instances, the intronic cassette may be located in any configuration relative to the transgene. For example, the intronic cassette may be located upstream, or 5', of the transgene, i.e. between the promoter and the initiation codon for the transgene. As another example, the intronic cassette may be located within the transgene, i.e. flanked by two exons of the transgene. As another example, the intronic cassette may be located downstream of the transgene, e.g. if the transgene does not comprise a termination sequence, the intronic cassette may be placed downstream of the transgene coding sequence and upstream of an exogenous termination, e.g. polyadenylation, sequence. As another example, the intronic cassette may be separated from the transgene by an RES sequence. In other instances, the intronic cassette of the subject vectors is under the transcriptional control of a promoter that is different than the promoter that will mediate expression of the transgene. In other words, the expression cassette that comprises the intronic cassette may not comprise the transgene of interest, but rather, will be a separate expression cassette from the one that comprises the transgene.

As discussed above, the MIP vector is substantially free of any bacterial plasmid backbone sequences other than those sequences comprised by the intronic cassette. In other words, the vector is devoid of a bacterial origin of replication and selectable marker outside the intron and has no more than 50 nt, no more than 40 nt, no more than 25 nt, no more than 10 nt, no more than 5 nt bacterial sequence derived from the plasmid backbone. In some instances, a mini-intronic plasmid vector is a vector that is substantially free of any bacterial sequences other than those comprised by the intronic cassette, i.e. the plasmid has no more than 50 nt, no more than 40 nt, no more than 25 nt, no more than 10 nt, no more than 5 nt bacterial sequence derived from the plasmid backbone. In some instances, as when the expression cassette comprises the intronic cassette, a mini-intronic plasmid may be said to be substantially free of any sequences other than the expression cassette comprising a transgene and intronic cassette, i.e. the plasmid has no more than 50 nt, no more than 40 nt, no more than 25 nt, no more than 10 nt, no more than 5 nt sequence. In some instances, it may be said that a mini-intronic plasmid vector is a vector that consists essentially of an expression cassette comprising a transgene and an expression cassette comprising an intronic cassette. In some instances, it may be said that a mini-intronic plasmid vector is a vector that consists essentially of an expression cassette comprising a promoter, a transgene, a termination sequence, and an intronic cassette. In some instances, it may be said that a mini-intronic plasmid vector is a vector that consists essentially of an expression cassette that consists essentially of a promoter, a transgene, a termination sequence, and an intronic cassette.

Generally, the overall length of the subject MIP vectors is sufficient to include the desired elements as described herein, but not so long as to prevent or substantially inhibit to an unacceptable level the ability of the vector to enter the target cell upon contact with the cell, e.g., via systemic administration to the host comprising the cell, or the ability of the expression cassette to express the transgene of interest. As such, the MIP vector is generally at least about 0.3 kb long, often at least about 1.0 kb long, where the vector may be as long as 5 kb or longer, in some instances 10 kb or 20 kb or longer, but in certain embodiments do not exceed this length. Any convenient method may be employed, e.g. as known in the art or described below, to determine if a vector is able to enter a cell and if the transgene is able to be expressed from the vector.

Mini-intronic plasmid vectors may be prepared in any of a number of ways using standard molecular biology techniques. For example, an origin of replication and selectable marker may be cloned into the endogenous intron of a transgene of interest, e.g. a transgene comprised by an expression cassette on a cloning vector, to create an intronic cassette, and the origin of replication and selectable marker of the cloning vector removed by restriction endonuclease digestion and self-ligation. The mini-intronic plasmid vector may then be propagated in cells, and cells comprising the vector selected for using the selection marker in the intronic cassette. Alternatively, an intronic cassette comprising a polynucleotide comprising an origin of replication and a selectable marker flanked by a splice donor sequence and a splice acceptor sequence may be isolated from a vector by excision by, e.g. restriction endonuclease digestion; the intronic cassette may be purified by, e.g. gel purification; the purified intronic cassette may be inserted into the expression cassette of a vector comprising the transgene; and the origin of replication and selectable marker of the cloning vector removed by restriction endonuclease digestion and self-ligation. The MIP vector may then be propagated in cells, and cells comprising the vector selected for using the selection marker in the intronic cassette. Any nucleic acid vector that is capable of transferring a gene of interest into target cells may be modified to become a MIP vector. As another alternative, a transgene of interest may be cloned into a vector comprising an intronic cassette operably linked to a promoter, such that the cloned transgene is also operably linked to the promoter, i.e. the transgene and intronic cassette will be transcribed into a single pre-mRNA. The mini-intronic plasmid vector may then be propagated in cells, and cells comprising the vector selected for using the selection marker in the intronic cassette. Any of these or any other approaches may be employed, e.g. as known the art or as described below and in the attached figures.

In some instances, the MIP vector that is created will be a linear nucleic acid vector. In other instances, the MIP vector that is created will be a circular nucleic acid. In some instances, the MIP vector that is created may be maintained extrachromosomally, or "episomally" in the target cell, i.e., as a linear or circular nucleic acid that does not integrate into the target cell genome. For example, a MIP vector may be created by modifying a non-integrating vector, e.g. a minicircle vector, or a non-integrating recombinant viral vector, e.g. a recombinant adenovirus or recombinant cytomegalovirus. In other instances, the MIP vector that is created may integrate into the genome of the host, i.e., as a linear or circular nucleic acid that integrates into the host genome. For example, a MIP vector may be created by modifying an integrating vector, e.g. a transposon-based vector (e.g. the Sleeping Beauty vector), or an integrating recombinant viral vector, e.g. a retrovirus, e.g. a recombinant lentivirus or phage. By a "recombinant virus" or a "recombinant viral vector", it is meant a virus, e.g. of the genus adenoviridiae, cytomegaloviridiae, lentivirus, that is capable of infecting a cell whose viral genome has been modified through conventional recombinant DNA techniques. Non-limiting examples of recombinant viruses that are commonly used in the art to transfer genes of interest into a target cell, e.g. in gene therapy, include recombinant adenoviruses ("Ad", or "Adv"), e.g. Ad2 and Ad5, as described for example in Curiel, D T and Douglas J T (2002) Adenoviral Vectors for Gene Therapy (Elsevier Inc.); recombinant adeno-associated viruses ("AAV"), e.g. AAV1, AAV2, AAV3, AAV4, AAV5, AAV6, AAV7, AAV8, AAV9, AAV10, AAV11, and AAV12, as described for example in Flotte, TR and Berns, KI. (2005) Adeno-associated viral vectors for gene therapy (Elsevier B.V.); and recombinant lentiviral vectors, as described for example in Trono, D (2003) Lentiviral Vectors, Vol. 261. (New York: Springer-Verlag). Methods of modifying, packaging, and purifying these and other recombinant viral vectors are well known in the art, see, e.g., Curiel and Douglas, supra; Flotte and Berns, supra; Trono, supra, and Machida (2003) Viral Vectors for Gene Therapy: Methods and Protocols. (New Jersey: Humana Press Inc.), the full disclosures of which are incorporated herein by reference.

Methods

Transgene expression from mini-intronic plasmid vectors finds use in many applications, including therapeutic applications such as in gene therapy; synthesis applications such as in the synthesis of peptides, proteins, and RNAs, e.g. for research or therapeutic purposes; and research applications, such as in the production of transgenic cells and animals.

In some applications, MIPs are employed to express one or more transgenes (referred to hereafter as "a transgene") in cells in vitro, e.g. for research purposes or for the synthesis of transgene product in vitro, or ex vivo, e.g., to produce genetically modified cells that can be reintroduced into an individual. Cells may be mitotic cells or post-mitotic cells, and include such cells of interest as pluripotent stem cells, e.g. ES cells, iPS cells, and embryonic germ cells; and somatic cells, e.g. fibroblasts, hematopoietic cells, neurons, muscle cells, bone cells, vascular endothelial cells, gut cells, and the like, and their lineage-restricted progenitors and precursors. Cells may be from any mammalian species, e.g. murine, rodent, canine, feline, equine, bovine, ovine, primate, human, etc. Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro.

If the cells are primary cells, they may be harvest from an individual by any convenient method. For example, cells, e.g. blood cells, e.g. leukocytes, may be harvested by apheresis, leukocytapheresis, density gradient separation, etc. As another example, cells, e.g. skin, muscle, bone marrow, spleen, liver, pancreas, lung, intestine, stomach tissue, etc. may be harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

MIP vectors may be provided directly to the subject cells. In other words, the target cells are contacted with MIP vector comprising the nucleic acid of interest such that the vector is taken up by the cells. Methods for contacting cells with nucleic acid vectors, such as electroporation, calcium chloride transfection, lipofection, and infection, are well known in the art. For example, a circular or linear nucleic acid MIP vector may be introduced into a target cell by formulating the vector into liposomes using an agent such as lipofectamine and contacting the cells with the liposomes ("lipofection"). As another example, a circular or linear nucleic acid vector may be electroporated into a target cell by contacting the cell with vector and applying an electrical field to increase the permeability of the cell membrane. As another example, a viral MIP vector may be introduced into a target cell by infecting the cell with viral particles comprising the vector. Typically, such viral particles are prepared by growing the vector in a packaging cell line, and purifying viral particles comprising the MIP vector packaged into viral capsids by the packaging cell line. Recombinant viruses, e.g. adenoviruses, cytomegaloviruses, retroviruses, etc., cell lines useful for their packaging into capsids, methods of introducing the subject MIP viral vectors into packaging cell lines, methods of collecting the viral particles that are generated by the packaging lines, and methods of infecting cells with viral particles in vitro or in vivo are well known in the art.

MIP vectors are typically provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The MIP may be provided to the subject cells one or more times, e.g. one time, twice, three times, or more than three times, and the cells allowed to incubate with the MIP for some amount of time following each contacting event e.g. 16-24 hours, after which time the media is replaced with fresh media and the cells are cultured further.

In cases in which two or more different coding sequences, i.e. transgenes, are provided to the cell, i.e. a cocktail of transgenes, the transgenes may be provided simultaneously, e.g. as two MIP vectors delivered simultaneously, or as a single MIP comprising the coding sequences for both transgenese. Alternatively, they may be provided consecutively, e.g. the first transgene being provided on a first MIP vector, followed by the second transgene on a second MIP vector, etc. or vice versa.

Typically, the MIP vector is provided to the cells in an amount effective to induce expression of the transgene in the cells. By an effective amount of MIP, it is meant the amount to induce a 10-fold increase or more in the level of transgene expression observed relative to a negative control, e.g. a cell contacted with an empty MIP, i.e. a MIP that does not comprise the transgene. That is to say, an effective amount or dose of MIP vector will induce a 10-fold increase, a 20-fold increase, a 50-fold increase or more in the amount of expression of a transgenic sequence observed, in some instances a 100-fold (2 log) increase, a 500-fold increase or more, sometimes a 1000-fold (3 log) or 10,000-fold (4 log) increase or more in the amount of recombination observed. The amount of expression may be measured by any convenient method, for example, Northern blot, Western blot, ELISA, FACS (fluorescence activated cell sorting), etc.

Contacting the cells with the MIP vector may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Following the methods described above, persistent, high level expression of a transgene may be achieved in vitro or ex vivo. In some embodiments, e.g. when a selectable protein is expressed, the population of cells may be enriched for those transformed by the MIP by separating the transformed cells from the remaining population. Separation may be by any convenient separation technique appropriate for the selectable protein used. For example, if a fluorescent marker is expressed, cells may be separated by fluorescence activated cell sorting, whereas if a cell surface marker is expressed, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the transformed cells.

Cell compositions that are highly enriched for transformed cells are achieved in this manner. By "highly enriched", it is meant that transformed cells will be 70% or more, 75% or more, 80% or more, 85% or more, 90% or more of the cell composition, for example, about 95% or more, or 98% or more of the cell composition. In other words, the composition may be a substantially pure composition of transformed cells, i.e. comprising MIPs.

Cells expressing the transgene of interest produced by the methods described herein may be used immediately. Alternatively, the cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The transformed cells may be cultured in vitro under various culture conditions. The cells may be expanded in culture, i.e. grown under conditions that promote their proliferation, and preferably maintain the mini-intronic plasmid. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the regulatory T cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Cells that have been transformed with MIP vector to express a transgene of interest may be transplanted to a subject for purposes such as gene therapy, e.g. to treat a disease or as an antiviral, antipathogenic, or anticancer therapeutic, for the production of genetically modified organisms in agriculture, or for biological research. The subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals, e.g. murine, lagomorpha, etc. may be used for experimental investigations.

Cells may be provided to the subject alone or with a suitable substrate or matrix, e.g. to support their growth and/or organization in the tissue to which they are being transplanted. Usually, at least $1\times10^3$ cells will be administered, for example $5\times10^3$ cells, $1\times10^4$ cells, $5\times10^4$ cells, $1\times10^3$ cells, $1\times10^6$ cells or more. The cells may be introduced to the subject via any of the following routes: parenteral, subcutaneous, intravenous, intracranial, intraspinal, intraocular, or into spinal fluid. The cells may be introduced by injection, catheter, or the like. Examples of methods for local delivery, that is, delivery to the site of injury, include, e.g. through an Ommaya reservoir, e.g. for intrathecal delivery (see e.g. U.S. Pat. Nos. 5,222,982 and 5,385,582, incorporated herein by reference); by bolus injection, e.g. by a syringe, e.g. into a joint; by continuous infusion, e.g. by cannulation, e.g. with convection (see e.g. US Application No. 20070254842, incorporated here by reference); or by implanting a device upon which the cells have been reversibly affixed (see e.g. US Application Nos. 20080081064 and 20090196903, incorporated herein by reference).

The number of administrations of treatment to a subject may vary. Introducing the transgene-expressing cells into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated.

In some applications, MIP vectors are employed to express transgenes in cells in vivo. In these in vivo embodiments, the MIP vectors are administered directly to the individual. The individual may be any mammalian species, e.g. murine, rodent, canine, feline, equine, bovine, ovine, primate, human, etc. The target cells may be mitotic cells or post-mitotic cells, and include, e.g. fibroblasts, hematopoietic cells, neurons, muscle cells, bone cells, vascular endothelial cells, gut cells, and the like, and their lineage-restricted progenitors and precursors.

MIP vectors may be administered to an individual by any of a number of well-known methods in the art for the administration of nucleic acids to a subject. The MIP vector can be incorporated into a variety of formulations. More particularly, the MIP vectors of the present invention can be formulated into pharmaceutical compositions by combination with appropriate pharmaceutically acceptable carriers or diluents.

Pharmaceutical preparations are compositions that include one or more mini-intronic plasmids present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the mini-intronic plasmids can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as brakykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

Typically, an effective amount of MIPs are provided. As discussed above with regard to ex vivo methods, an effective amount or effective dose of a MIP in vivo is the amount to induce a 10 fold increase or more in the amount of expression of a transgene relative to a negative control, e.g. a cell contacted with an empty vector. The amount of recombination may be measured by any convenient method, e.g. as described above and known in the art. The calculation of the effective amount or effective dose of a MIP to be administered is within the skill of one of ordinary skill in the art, and will be routine to those persons skilled in the art. Needless to say, the final amount to be administered will be dependent upon the route of administration and upon the nature of the disorder or condition that is to be treated.

The effective dose of a MIP for introduction into cells may be empirically determined by one of skill in the art. For example, MIPs may be provided to cells at a concentration of at least about 1 ng for $10^6$ cells, about 10 ng for $10^6$ cells, about 100 ng for $10^6$ cells, about 1 μg for $10^6$ cells, about 5 μg for $10^6$ cells, or more. Typically high concentrations are not deleterious. The effective amount given to a particular patient will depend on a variety of factors, several of which will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, the MIP may be obtained from a suitable commercial source. As a general proposition, the total pharmaceutically effective amount of the MIP administered parenterally per dose will be in a range that can be measured by a dose response curve.

MIP-based therapies, i.e. preparations of mini-intronic plasmid vectors to be used for therapeutic administration, must be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The MIP-based therapy may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required.

Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Utility

As discussed above, the subject mini-intronic plasmid vectors may be used to achieve persistent, high level expression of a transgene of interest in mammalian cells. By high level expression, it is meant that the transgene is expressed by a host cell at a level that is 50-fold greater, 100-fold (2-log) greater, 1000-fold (3-log) greater, or 10,000 fold (4-log) greater or more, within the first 1, 2, or 3 days following transformation than in the absence of vector. By persistent, it is meant that high level expression of the transgene persists for 2 weeks or more, for example, 3 weeks or more, 5 weeks or more, 7 weeks or more, 9 weeks or more, 13 weeks or more, 18 weeks or more, 6 months or more, e.g. 12 months. In other words, the expression level of the transgene does not decrease more than 100-fold, more usually not more than 50-fold, in some instances, not more than 10-fold in the 2 weeks or more, i.e. 3 weeks, 5 weeks, 7 weeks, 9 weeks or more, 13 weeks or more, 18 weeks or more, 6 months or more following transformation from levels observed within the first 1, 2, or 3 days. This is in contrast to plasmids, this is, circular vectors comprising plasmid backbone sequences, e.g. bacterial origin of replication and selectable marker, that are not in an intron, i.e., that are not flanked by splicing sequences or other elements that promote splicing. For example, as demonstrated in the working examples below, whereas expression of a transgene from a plasmid is expected to decrease by 50-fold or more from initial levels by 3 weeks after introduction into a cell, expression of a transgene from a MIP vector may be expected to decrease less than 10-fold from initial levels in that same time period. As such, the subject MIP vectors may provide for expression that is 5-fold greater or more, e.g., 10-fold greater more, 50-fold greater or more, in some instances 100-fold greater, than expression from a vector comprising an origin of replication and selectable marker that are not in an intron, i.e. a plasmid. In some instances, the subject methods comprise the step of measuring the expression level of the transgene, e.g. 3 weeks or more after introducing the MIP vector into the cell, wherein the expression level is at least 10-fold more than a transgene expressed from a plasmid comprising an origin of replication and a selectable that are not in an intron.

The inclusion of the bacterial origin of replication and selectable marker on the MIP provides several advantages to MIPs as compared to minicircle vectors. For example, these elements allow the plasmid to be propagated in bacteria. Additionally, as demonstrated in the working examples below, if the PR sequence (FIG. 7A, SEQ ID NO:5) is used as the selectable marker on the MIP, more robust expression may be achieved. For example, inclusion of the PR sequence may enhance expression of the transgene 2 to 5-fold or more, e.g. 2-fold, 3-fold, 4-fold, 5-fold, or more, over expression from a minicircle vector.

The subject compositions and methods find use in a variety of applications in which the introduction of a nucleic acid into a target cell is desired. Applications in which the subject vectors and methods find use include research applications, RNA or polypeptide synthesis applications, and therapeutic applications. Each of these representative categories of applications is described separately below in greater detail.

Research Applications

Examples of research applications in which the subject compositions and methods find use include applications designed to characterize a particular gene. In such applications, the subject vectors may be employed to introduce and express a gene of interest in a target cell and the resultant effect of the inserted gene on the cell's phenotype is observed. Alternatively, the subject vectors may be employed to introduce and express a nucleic acid sequence encoding an shRNA or siRNA that is specific for a gene of interest in a target cell, and the resultant effect of inhibiting the expression of the target gene on the cell's phenotype is observed. In this manner, information about the gene's activity and the nature of the product encoded thereby can be deduced. One can also employ the subject methods to produce models in which overexpression and/or misexpression of a gene of interest is produced in a cell and the effects of this mutant expression pattern are observed.

RNA and Polypeptide Synthesis Applications

In addition to the above research applications, the subject compositions and methods also find use in the synthesis of polypeptides, e.g. proteins of interest, and RNAs, e.g. siRNA or miRNA of interest. In such applications, a MIP vector that includes a gene encoding the polypeptide of interest in combination with requisite and/or desired expression regulatory sequences, e.g. promoters, etc., (i.e. an expression module) is introduced into the target cell, e.g. via in vitro contacting of the unicellular organism with the MIP, or via in vivo administration to the multicellular organism in which the target cell resides, that is to serve as an expression host for expression of the polypeptide. Following administration, the transformed cell is maintained under conditions sufficient for expression of the transgene. The expressed RNA or protein is then harvested, and purified where desired, using any convenient protocol.

As such, the subject methods provide a means for at least enhancing the amount of a protein or RNA of interest in a unicellular or multicellular organism. The term 'at least enhance' includes situations where the methods are employed to increase the amount of a protein or RNA in a unicellular or multicellular organism where a certain initial amount of protein or RNA is present prior to in vivo administration of the vector. The term 'at least enhance' also includes those situations in which the unicellular or multicellular organism includes substantially none of the protein or RNA prior to administration of the vector. By "at least enhance" is meant that the amount of the particular protein or RNA present in the host is increased by at least about 2 fold, usually by at least about 5 fold and more usually by at least about 10 fold. As the subject methods find use in at least enhancing the amount of a protein or RNA present in a unicellular or multicellular organism, they find use in a variety of different applications, including agricultural applications, pharmaceutical preparation applications, e.g. large scale production of protein or RNA therapeutic agents, and the like, as well as therapeutic applications, described in greater detail infra.

Therapeutic Applications

The subject methods and compositions also find use in therapeutic applications, in which the vectors are employed to introduce a therapeutic nucleic acid, e.g., gene, into a target cell, i.e., in gene therapy applications, to provide for persistent expression of the product encoded by the nucleic acid present on the vector. The subject vectors may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, β-globin, low-density lipoprotein receptor, adenosine deaminase, purine nucleoside phosphorylase, sphingomyelinase, glucocerebrosidase, cystic fibrosis transmembrane conductor regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like, where the particular coding sequence of the above proteins that is employed will generally be the coding sequence that is found naturally in the host being treated, i.e., human coding sequences are employed to treat human hosts. Cancer therapeutic genes that may be delivered via the subject methods include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

The subject methods and compositions also find use in the expression of RNA products, e.g., shRNA, miRNA, antisense RNA, ribozymes etc., as described in Lieber et al., "Elimination of hepatitis C virus RNA in infected human hepatocytes by adenovirus-mediated expression of ribozymes," J. Virol. (1996 December) 70(12):8782-91; Lieber et al., "Related Articles Adenovirus-mediated expression of ribozymes in mice," J. Virol. (1996 May) 70(5):3153-8; Tang et al., "Intravenous angiotensinogen antisense in AAV-based vector decreases hypertension," Am J. Physiol. (1999 December) 277(6 Pt 2):H2392-9; Horster et al. "Recombinant AAV-2 harboring gfp-antisense/ribozyme fusion sequences monitor transduction, gene expression, and show anti-HIV-1 efficacy, Gene Ther. (1999 July) 6(7):1231-8; and Phillips et al., "Prolonged reduction of high blood pressure with an in vivo, nonpathogenic, adeno-associated viral vector delivery of AT1-R mRNA antisense," Hypertension. (1997 January) 29(1 Pt 2):374-80. As such, the subject methods can be used to deliver therapeutic RNA molecules, e.g., antisense, ribozyme, etc., into target cells of the host.

The subject methods and compositions also find use in the expression in somatic cells of genes that encode reprogramming factors or transdifferentiation factors. By "reprogramming factors", it is meant factors, e.g. proteins, RNAs, etc., for example, Oct3/4, Sox2, Klf4, c-Myc, Nanog, Lin-28, miR302/367, that reprogram somatic cells to become induced pluripotent stem cells (iPS cells), e.g. human iPS cells. By "transdifferentiation factors" it is meant factors, e.g. proteins, RNAs, etc., that induce somatic cells to transdifferentiate into induced somatic cells of another lineage without undergoing an intermediate pluripotent state; see, e.g. PCT Application Publication No. WO 2011/091048, the full disclosure of which is incorporated herein by reference. In addition, the subject methods and compositions also find use in the expression of genes in stem or progenitor cells that direct the development of stem or progenitor cells into desired cell fates. iPS cells and somatic cells that are induced to differentiate from somatic cells or pluripotent cells find many experimental and therapeutic uses, as known in the art.

An important feature of the subject methods, as described supra, is that the subject methods may be used for in vivo gene therapy applications. By in vivo gene therapy applications is meant that the target cell or cells in which expression of the therapeutic gene is desired are not removed from the host prior to contact with the vector system. In contrast, the subject vectors are administered directly to the multicellular organism and are taken up by the target cells, following which expression of the gene in the target cell occurs. Another important feature is that the resultant expression is persistent and occurs without integration of the vector DNA into the target cell genome.

Reagents, Devices and Kits

Also provided are reagents, devices and kits thereof for preparing one or more of the above compositions and for practicing one or more of the above-described methods. The subject reagents, devices and kits thereof may vary greatly. Reagents and devices of interest include those mentioned above with respect to methods of making mini-intronic plasmid vectors. For example, reagents may include vectors, e.g. circular or linear nucleic acid molecules, comprising intronic cassettes for cloning mini-intronic cassettes into transgenes. Vectors comprising mini-intronic cassettes, e.g. vectors comprising a mini-intronic cassette operably linked to a promoter, may also be used as receiving vectors into which transgenes of interest may be cloned to create mini-intronic vectors. Other reagents include frozen cells for transformation with the mini-intronic plasmid vectors or vector precursors, and reagents that are specific for the selectable marker on the intronic cassette and that may be used to select transformed cells.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

The bacterial backbone sequences contained within a canonical plasmid DNA dampen exogenous transgene expression by 10 to 1000 fold over a period of a few weeks following transfection into quiescent tissues such as the liver (Chen et al., Minicircle DNA vectors devoid of bacterial DNA result in persistent and high-level transgene expression in vivo. *Mol Ther* 8, 495-500 (2003); Chen et al., Improved production and purification of minicircle DNA vector free of plasmid bacterial sequences and capable of persistent transgene expression in vivo. *Hum Gene Ther* 16, 126-131 (2005); Bigger et al., An araC-controlled bacterial cre expression system to produce DNA minicircle vectors for nuclear and mitochondrial gene therapy. *J Biol Chem* 276, 23018-23027 (2001); Darquet et al., A new DNA vehicle for nonviral gene delivery: supercoiled minicircle. *Gene Ther* 4, 1341-1349 (1997); Mayrhofer et al., Minicircle-DNA production by site specific recombination and protein-DNA interaction chromatography. *J Gene Med* 10, 1253-1269 (2008); Schakowski et al., Minimal size MIDGE vectors improve transgene expression in vivo. *In Vivo* 21, 17-23 (2007)). Minicircle DNA vectors devoid of bacterial plasmid backbone sequences overcome transgene silencing providing persistent transgene expression. However, the production of minicircle vectors is a multistep, time-consuming process. Reported here is the development of an alternative vector propagation process, in which the essential bacterial elements for plasmid replication and selection are placed within an engineered intron contained within the eukaryotic expression cassette. As with the minicircle vector, the mini-intronic plasmid (MIP) vector system overcomes transgene silencing observed with plasmids but in addition provides more than 10-times higher levels of transgene expression compared to minicircle vectors containing the same expression cassette in vivo and in vitro. These improved vectors benefit all studies involving gene transfer/therapy approaches.

Materials and Methods

Materials. The NTC8385-EGFP vector (Nature Technology Corporation) was used to isolate PR sequence (containing trpA terminator, pUC bacterial replication origin and RNA-OUT selectable marker). NTC4862 DH5α competent cells (Nature Technology Corporation) were used to produce MIP vectors.

Vector construction. pRHB (pRSV-hAAT-bpA) and MC.RHB were previously described (Chen et al., Minicircle DNA vectors devoid of bacterial DNA result in persistent and high-level transgene expression in vivo. *Mol Ther* 8, 495-500, (2003)). MC.RH(intron2)B was generated by inserting a RSV-hAAT(exon 1, 2-intron2-exon3,4,5)-bpA fragment into the minicircle producing plasmid (Kay et al., A robust system for production of minicircle DNA vectors. *Nat Biotechnol* 28, 1287-1289, (2010)). The PR sequence was isolated from NTC8385-EGFP vector through PCR reaction with primer pairs 5'-GCCCGCCTAATGAGCGGGC-3' (SEQ ID NO:8) and 5'-GGCCGGGGTACCTAATGATTT-3' SEQ ID NO:9). A SalI restriction site was incorporated into both the 5' and 3' ends of PR sequence and was then ligated to XhoI linearized MC.RH(intron2)B to produce vector MIP.RHB. To make MIPse.RHB, a SspI restriction site was incorporated into the 5' end of PR sequence and a SalI site was incorporated into the 3' end of PR sequence. Both SspI and Xho/were used to remove most of the intron2 sequences in MC.RH(intron2)B, and the remaining sequences were then ligated with SspI and SalI digested PR sequence to form MIPse.RHB. The In-Fusion PCR cloning system (Clontech) was used to generate the MIPsne.RHB construct. Primer pairs 5'-TTCCCCTCTCTCCAGGTCTGCCAGCTTACATTTACC-3' (SEQ ID NO:10) and 5'-GTTGAGCAACCTTAC-CTTCTGTCTTCATTTTCCAGG-3' (SEQ ID NO:11) (underlined sequences were the homologous sequences used for In-Fusion ligation) were used to PCR amplify the In-Fusion ligation fragment that contains hAAT (exon 4, 5)-bpA-RSV-hAAT (exon 1, 2, 3) from MC.RHB and primer pairs 5'-GTAAGGTTGCTCAACCAGCC-3' (SEQ ID NO:12) and 5'-CTGGAGAGAGGGGAAGGTG-3' (SEQ ID NO:13) were used to PCR amplify PR sequence with intron2 splicing sites from MIPse.RHB. The two PCR amplified fragments were then ligated together through the In-Fusion system to generate MIPsne.RHB. The optimized intron with a pUC origin and RNA-OUT sequence ("OIPR" sequence, FIG. 2Aa) was generated through PCR reactions. An NheI site was incorporated into the 5' end of OIPR and a SpeI site was incorporated into the 3' end of OIPR. An NheI site was incorporated into MC.RHB right before the start codon of the hAAT cDNA. Then the NheI linearized MC.RHB was ligated with NheI, SpeI double digested OIPR to build MIP.5'OIPR.RHB. To form MIP.3'OIPR.RHB, a PstI site was incorporated into each end of OIPR. Then a PstI linearized (after stop codon of hAAT cDNA and before bpA) MC.RHB fragment was used to ligate with PstI digested OIPR to produce MIP.3'OIPR.RHB. An RSV-hAAT-bpA linearized fragment was generated by SpeI single digestion of MC.RHB. A PR sequence containing SpeI on each end was amplified through PCR reaction. These two SpeI digested fragments were ligated together to make the pMIP.RHB construct. The MC.5'Ointron2.RHB vector was built through In-Fusion ligation. Primer pairs 5'-AGCAGGTAAGGTTGCTCAA-CCAGCC-3' (SEQ ID NO:14) and 5'-TTCAGCTTGCGGCCTGGAGAGAGGGGAAGGTG-3' (SEQ ID NO:15) were used to amplify hAAT intron 2 and primer pairs 5'-AGGCCGCAAGCTGAAGCGT-3' (SEQ ID NO:16) and 5'-GCAACCTTACCTGCTGTGTG-3' (SEQ ID NO:17) were used to generate hAAT-bpA-RSV sequence that containing optimized splicing sites before the hAAT start codon. The In-Fusion ligation of these two fragments resulted in the MC.5'Ointron2.RHB vector.

MIP vector production. Ligation reactions were transformed into NTC4862 DH5α competent cells. Cells were then plated on 6% sucrose solid media (Nature Technology Corporation's NTC vector user manual) and propagated at 30° C. for 24 to 48 hours. Colonies were picked up for miniprep. 100 ul bacterial culture of positive mini-prep was then inoculated into 100 ml 6% sucrose liquid media and incubate for 16 to 18 hours at 37° C. The overnight culture carries MIP vector was then produced through conventional plasmid vector preparing procedure by using QIAGEN plasmid MAXI prep kit.

Animal studies. All animal procedures were performed under the guidelines set forth by the NIH and after approval from the Stanford Animal Care Committee. Six to eight week old female C57BL/6J mice purchased from Jackson Laboratory were used for DNA vector infusion. To ensure the same molar amount of DNA was injected into each animal, 3.63 μg/kb DNA was used for various sized constructs in FIG. 1B, FIG. 2B and FIG. 3D. 1.8 μg/kb DNA was used for various sized constructs in FIG. 3B. Each DNA construct was diluted into 1.8 ml 0.9% NaCl for each animal, and was delivered through hydrodynamic tail vein injection. Five animals were tested for each DNA construct in each tested experimental group. After DNA infusion, blood samples were collected periodically by a retro-orbital technique. The serum hAAT and the plasma hFIX levels were quantified by ELISA as described earlier (Yant et al., Somatic integration and long-term transgene expression in normal and haemophilic mice using a DNA transposon system. *Nat Genet* 25, 35-41, (2000)).

Southern blot analysis. The salt-out procedure was used to extract liver genomic DNA. Two representative animals from each treated group were selected. The liver genomic DNA of each animal was then digested with either BamHI alone or BamHI and PmII overnight at 37° C. BamHI cut the expression cassette once. BamHI, PmII double digestion cut the expression cassette twice. The digested genomic DNA was then extracted using phenol-chloroform. 20 μg phenol-chloroform extracted genomic DNA of each animal was loaded on 1% agar gel. Various amounts of the hAAT cDNA were also digested with BamHI and PmII, and then mixed with 20 μg non-infused mouse liver genomic DNA in each lane as copy number control. Southern blot membrane was hybridized with [P-32] dCTP-labeled BamHI and PmII double digested 600 bp hAAT cDNA fragment, and [P-32] dCTP-labeled 300 bp β-actin (PCR product by using forward primer 5'-ACGCGTCCAATTGCCTTTCT-3' (SEQ ID NO:18) and reverse primer 5'-CTCGAGGTTGAAGGTCTCAA-3' (SEQ ID NO:19)). The copy number calculation method was as previously described (Lu et al., The extragenic spacer length between the 5' and 3' ends of the transgene expression cassette affects transgene silencing from plasmid based vectors. *Mol Ther* (2012)). The Southern blot signal strength was measured using Quantity One software.

Quantitative PCR analysis. 100 ng BamHI digested genomic DNA (FIG. 1 C) and BamHI, PmII double digested genomic DNA (FIG. 2C) from each sample was used as the template for qPCR. One (for FIG. 1C) or two (for FIG. 2C) animal samples from each injection group were selected and two 20 μl reactions were performed for each animal sample. Various copy numbers (2E+8 copies to 20 copies) of double digested standard vector DNA along with 100 ng non-infused control genomic DNA per reaction were used to calculate a copy number standard curve. Forward primer 5'-AAG-GCAAATGGGAGAGACCT-3' (SEQ ID NO:20) and reverse primer 5'-TACCCAGCTGGACAGCTTCT-3' (SEQ ID NO:21) oligos were used to amplify 150 bp fragment from hAAT cDNA region. Forward primer 5'-TTGCTGACAG-GATGCAGAAG-3' (SEQ ID NO:22) and reverse primer 5'-TGATCCACATCTGCTGGAAG-3' (SEQ ID NO:23) oligos were used to amplify 150 bp fragment from β-actin as loading control. The tested transgene signal was then normalized to the β-actin signal. The mass of a single diploid copy of mouse genome is 5.88 pg. Thus 100 ng genomic DNA contains 17007 copies of diploid genome (1E+6 pg/5.88 pg). The average transgene copy number in 100 ng genomic DNA from each group was then divided by 17007 to achieve the transgene construct copy number in each cell. All calculations were based on methods described by the Applied Biosystems method, which may be found on the world wide web by inserting http:// followed by "www6.appliedbiosystems.com/support/tutorials/pdf/quant-_per.pdf" and by using the internet tool which may be found on the world wide web by inserting http:// followed by "www.uri.edu/research/gsc/resources/cndna.html." qPCR was performed using a Corbett Research RG6000 PCR instrument.

Northern blot analysis. hAAT transcript was detected by standard northern blotting methods, using total liver RNA isolated by TRIzol (Invitrogen). 20 μg total liver RNA was used for each sample. Two identical northern blots were prepared for each experiment. One northern blot was probed with a 220 bp long [P-32] dCTP-labeled hAAT cDNA probe to detect hAAT mRNA. 220 bp hAAT cDNA probe was generated through PCR by using primers 5'-GCCGTCTTCT-GTCTCGTGG-3' (SEQ ID NO:24) and 5'-AAGAAGATAT-TGGTGCTGTTGG-3' (SEQ ID NO:25). The other northern blot was probed with [P-32] dCTP-labeled β-actin probe to detect β-actin as loading control.

Reverse transcription (RT) reaction and following quantitative PCR (qPCR) reaction. RT reactions were performed according to the manual of SuperScript III First-Strand Synthesis System for RT-PCR from Invitrogen. cDNA synthesis was performed in the first step using 5 μg DNaseI treated liver total RNA sample primed with gene specific primer (RNA-OUT U, RNA-OUT D or hAAT D). The sequence of RNA-OUT U primer is 5'-GTAGAATTGGTAAAGAGAGTCG-3' (SEQ ID NO:26). The sequence of RNA-OUT D primer is 5'-GGTACCTAATGATTTTTATCAAAA-3' (SEQ ID NO:27). The sequence of hAAT D primer is 5'-TTATTTTTGGGTGGGATTCACC-3' (SEQ ID NO:28). The synthesized RNA-OUT cDNA was further quantified through qPCR with primers RNA-OUT qPCR U (5'-GGTAAAGAGAGTCGTGTAAAAT-3' (SEQ ID NO:29)) and RNA-OUT qPCR D (5'-GATTTTTATCAAAATCATTAAGTTAA-3' (SEQ ID NO:30)). The synthesized hAAT cDNA was further quantified through qPCR with primers hAAT qPCR U (5'-AAGGCAAATGGGAGAGACCT-3' (SEQ ID NO:31)) and hAAT qPCR D (5'-TACCCAGCTGGACAGCTTCT-3' (SEQ ID NO:32)). Linearized RNA-OUT DNA templates at the concentrations of 0.1 ng/μl, 0.01 ng/μl, 0.001 ng/μl, 0.001 ng/μl, 0.0001 ng/μl and 0.00001 ng/μl were used to setup qPCR standard. The results were further normalized by the amount of total RNA used for RT reaction.

Western blot analysis. hAAT expression in mouse serum and the HEK293 cell line was validated by Western blotting using a monoclonal anti-hAAT antibody (Abcam). Serum samples (20 μl/sample) from treated animals nine weeks after vector infusion along with non-treated animal sera were used to perform Western blot. 8×10E5 HEK293 cells were seeded in each well of a 6-well tissue culture plate one day before transfection. 4 ug of each DNA vector was transfected into each well according to the Lipofectamine 2000 Transfection Reagent manual from Invitrogen. Cell lysates were then harvested 24 hours after transfection and used for the study. hAAT protein was visualized using the monoclonal antibody (Abcam) at a 1:4,000 dilution.

Firefly luciferase in vivo imaging. D-luciferin (firefly) potassium salt was dissolved in DPBS to make 15 mg/ml injection solution. The luciferin injection solution was infused into tested mice through intraperitoneal (IP) injection. A dose of 10 μl/g mouse weight is used. The luciferase signal was examined at 10 minutes after injection by Xenogen IVIS 200 spectrum. The luciferase2 images in FIG. 5B were taken under the following settings: Em Filter=Open, Ex Filter=Block, Bin:(M)8, FOV:22.4, f4, 1 sec. Quantitation of signal was calculated using the Living Image 4.3 software.

HEK293 cell transfection. 1.6×10E5 HEK293 cells were seeded in each well of a 24-well tissue culture plate one day before transfection. 500 ul media was used in each well. For the experiments shown in FIG. 6B, the same molar amount of each DNA vector was co-transfected with pRSV.GFP DNA vector at the ratio of 3:1 into each well according to the Lipofectamine 2000 Transfection Reagent manual from Invitrogen. GFP expression was checked with a UV microscope 24 hours, 48 hours and 72 hours after transfection. Cell culture media was changed every 24 hours after transfection and the hAAT transgene levels in the media were tested through ELISA. The resulting total hAAT levels every 24 hours were divided by total cell number plated into each well. For the experiments shown in FIG. 5C, the same molar amount of each DNA vector was co-transfected with pRL-SV40 DNA vector at the ratio of 50:1 into each well. Transfected HEK293 cells were treated by Dual-Luciferase Reporter 1000 Assay System, and thehe firefly luciferase2 and renilla luciferase signals detected by VERITAS microplate luminometer.

Preparation of AAV. A standard calcium-phosphate triple-transfection method (Grimm, D, Production methods for gene transfer vectors based on adeno-associated virus serotypes. Methods 28, 146-157, (2002)) was used to produce the AAV8 vectors. Briefly, HEK293 cells were transfected with equal amounts of the following plasmids: the AAV packaging helper containing the rep and cap genes, the adenoviral helper pladeno5, and the p388-AC-For plasmid containing either the MIP.5'OIPR.RHB or the RHB expression cassette enclosed between AAV2 inverted terminal repeats. Each T225 (Corning, Corning, N.Y.) flask of HEK293 cells were transfected with 25 ug of each vector DNA. 3 days after transfection, the cells were harvested and subjected to a standard AAV purification procedure including two rounds of cesium chloride gradient ultracentrifugation for purification, ultrafiltration-diafiltration (Amersham, Piscataway, N.J.) for cesium chloride removal and particle concentration, and dot blot titration. The final viral preparations were kept frozen at −80° C. in phosphate-buffered saline containing 5% sorbitol.

Animal infusion with AAV. 1×10E11 VG (Vector Genome) AAV8 viruses diluted in 200 μl PBS (PH 7.4) were injected into each 6 to 8 week-old female C57BL/6 mouse (Jackson Laboratory Bar Harbor, Me.) through tail vein injection. 5 mice were injected in each group. All animal procedures were performed under the guidelines set forth by the NIH and after approval from the Stanford Animal Care Committee. Blood samples were collected at various time points (3 days, 5 days, 1 week, 2 weeks, 3 weeks, 4 weeks, 5 weeks, 10 weeks and 12 weeks) after infusion. Serum hAAT levels were determined through ELISA analysis.

Results

Plasmid bacterial backbone DNA contained in an intron provides sustained transgene expression in vivo. The "mini-intronic plasmid vector" or "MIP" contains a bacterial replication origin and selectable marker maintaining the juxtaposition of the 5' and the 3' ends of transgene expression cassette as in a minicircle. The additional advantages over the minicircle is that the preparation time is shorter (same time as a conventional plasmid), no antibiotic selection is required, and a specific bacterial host required for minicircle production (Kay et al., A robust system for production of minicircle DNA vectors. Nat Biotechnol 28, 1287-1289 (2010)) is unnecessary.

Figure 1B:
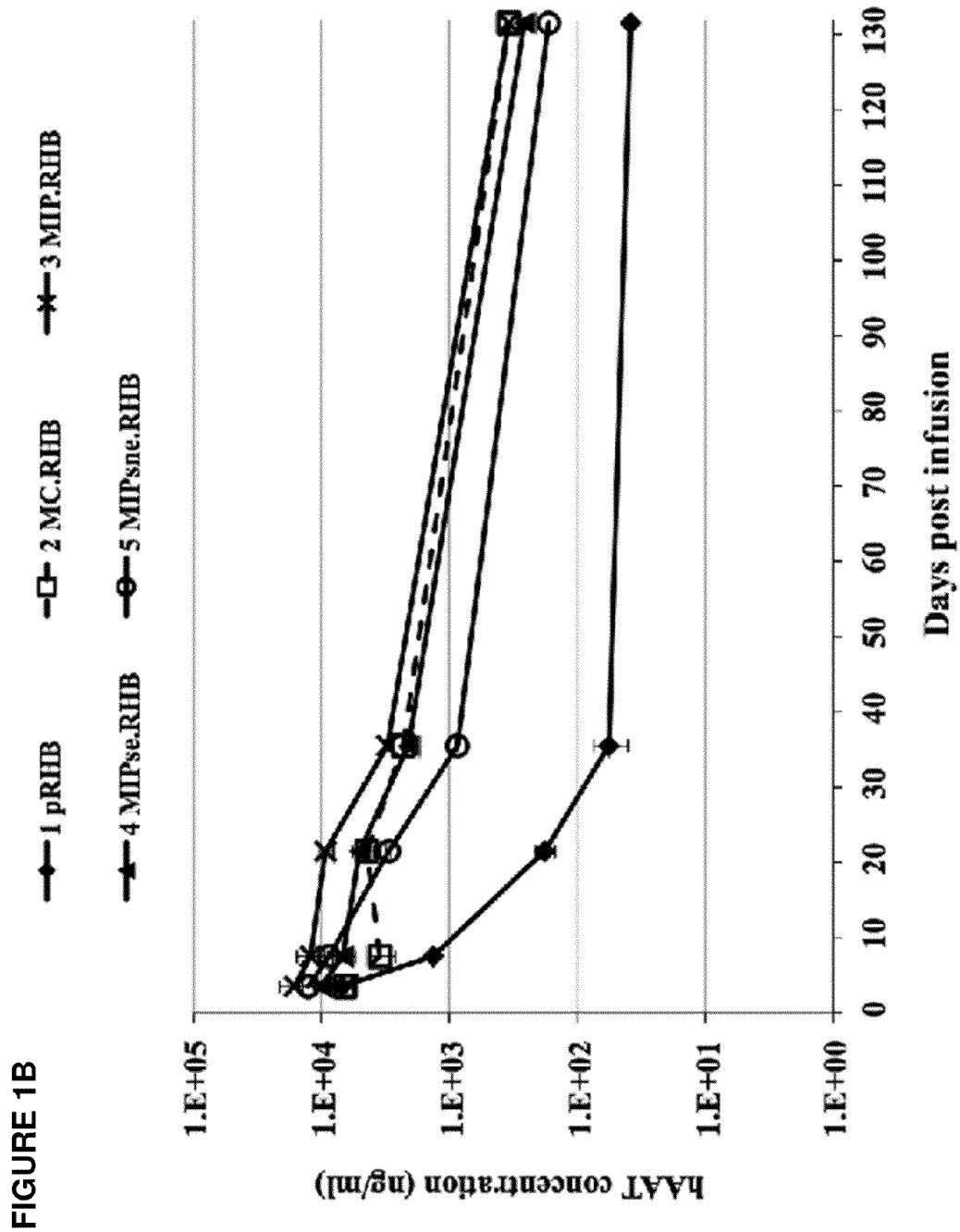

The specific vectors created utilized a high copy number pUC origin and antibiotic-free RNA-OUT selectable marker (PR sequence) (FIG. 1A(a), FIG. 7A) (Luke et al., Improved antibiotic-free DNA vaccine vectors utilizing a novel RNA based plasmid selection system. Vaccine 27, 6454-6459 (2009); Carnes et al., Critical design criteria for minimal antibiotic-free plasmid vectors necessary to combine robust RNA Pol II and Pol III-mediated eukaryotic expression with high bacterial production yields. J Gene Med 12, 818-831 (2010)). The 145 nucleotide RNA sequence is transcribed only in prokaryotes and represses expression of a chromosomally integrated constitutively expressed counter-selectable marker (SacB) in the host bacterial strain, allowing vector selection when grown in sucrose (Luke et al., Improved antibiotic-free DNA vaccine vectors utilizing a novel RNA based plasmid selection system. Vaccine 27, 6454-6459 (2009)). In our first set of constructs, the PR sequences were cloned into the native intron 2 of the human alpha 1-antitrypsin (hAAT) minigene (FIG. 1A(b), "MIP.RHB"). Additional constructs had the PR sequences inserted into a minimal intron 2 containing the splicing branch point and polypyrimidine tract (FIG. 1A(b), "MIPse.RHB" or "MIPsne.RHB"). In one vector, the shortened intron remained positioned at the exon 2 and 3 junction (endogenous location "MIPse.RHB"); in the other, it was placed between exon 3 and 4 (non-endogenous location "MIPsne.RHB"). These three MIP constructs along with a canonical bacterial backbone (BB) containing plasmid pRHB (silencing control) and BB minus minicircle MC.RHB (non-silencing control) were infused into the livers of 6-8 week-old C57BL/6 female mice through hydrodynamic tail vein injection, respectively and the serum hAAT transgene product was quantified at various time points (FIG. 1B). As observed in the past (Chen et al., Minicircle DNA vectors devoid of bacterial DNA result in persistent and high-level transgene expression in vivo. *Mol Ther* 8, 495-500 (2003); Lu et al., The extragenic spacer length between the 5' and 3' ends of the transgene expression cassette affects transgene silencing from plasmid based vectors. *Mol Ther* 20(11):2111-9 (2012)), pRHB resulted in high levels of serum hAAT shortly after vector administration, but then declined to very low levels during the next 2-3 weeks (FIG. 1B). In contrast, the expression from MC.RHB, MIP.RHB and MIPse.RHB constructs resulted in similar expression profiles (FIG. 1B). The MIPse.RHB, MC.RHB, and MIP.RHB vectors all expressed at 10-times higher levels than the pRHB canonical plasmid vector, although transgene expression from the MIPsne.RHB vector was slightly reduced compared to MC.RHB and MIP.RHB (FIG. 1B).

Figure 1C:
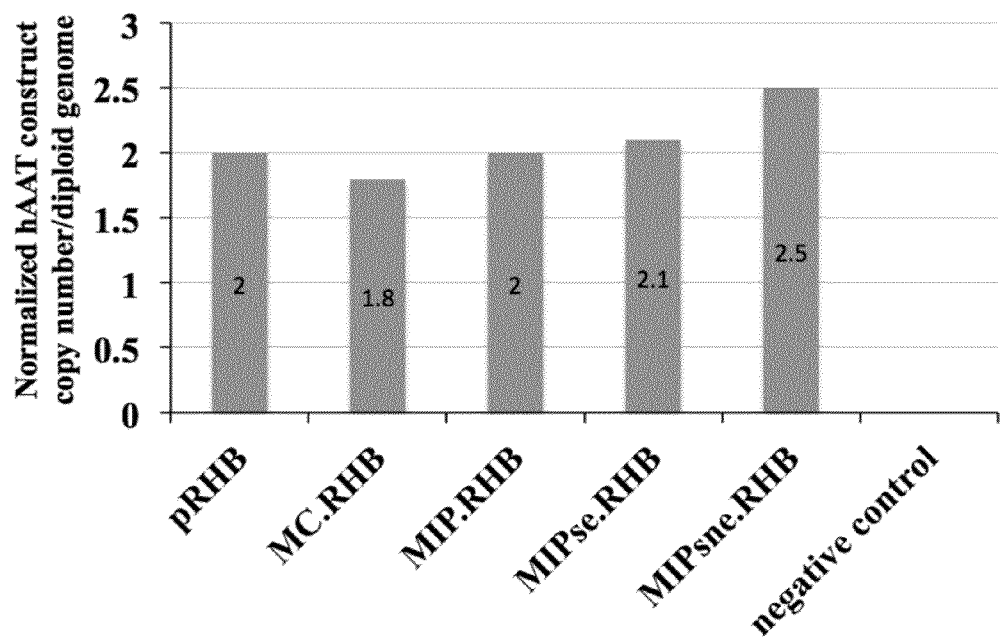
Figure 1D:
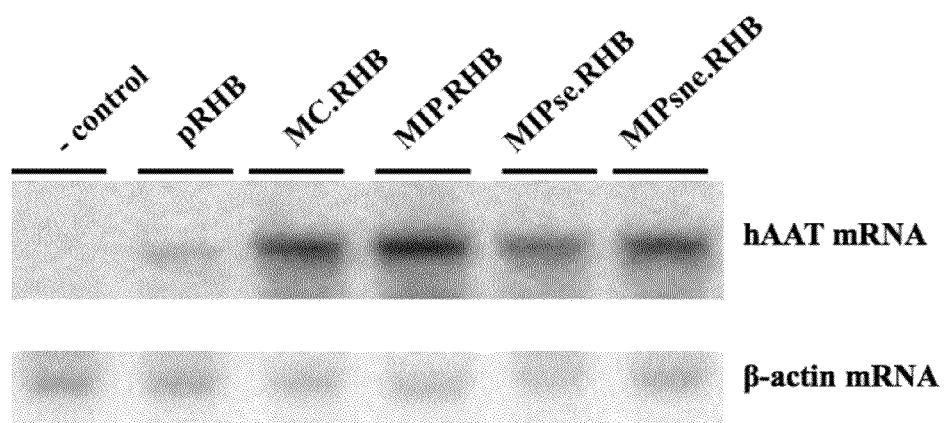
Figure 8:
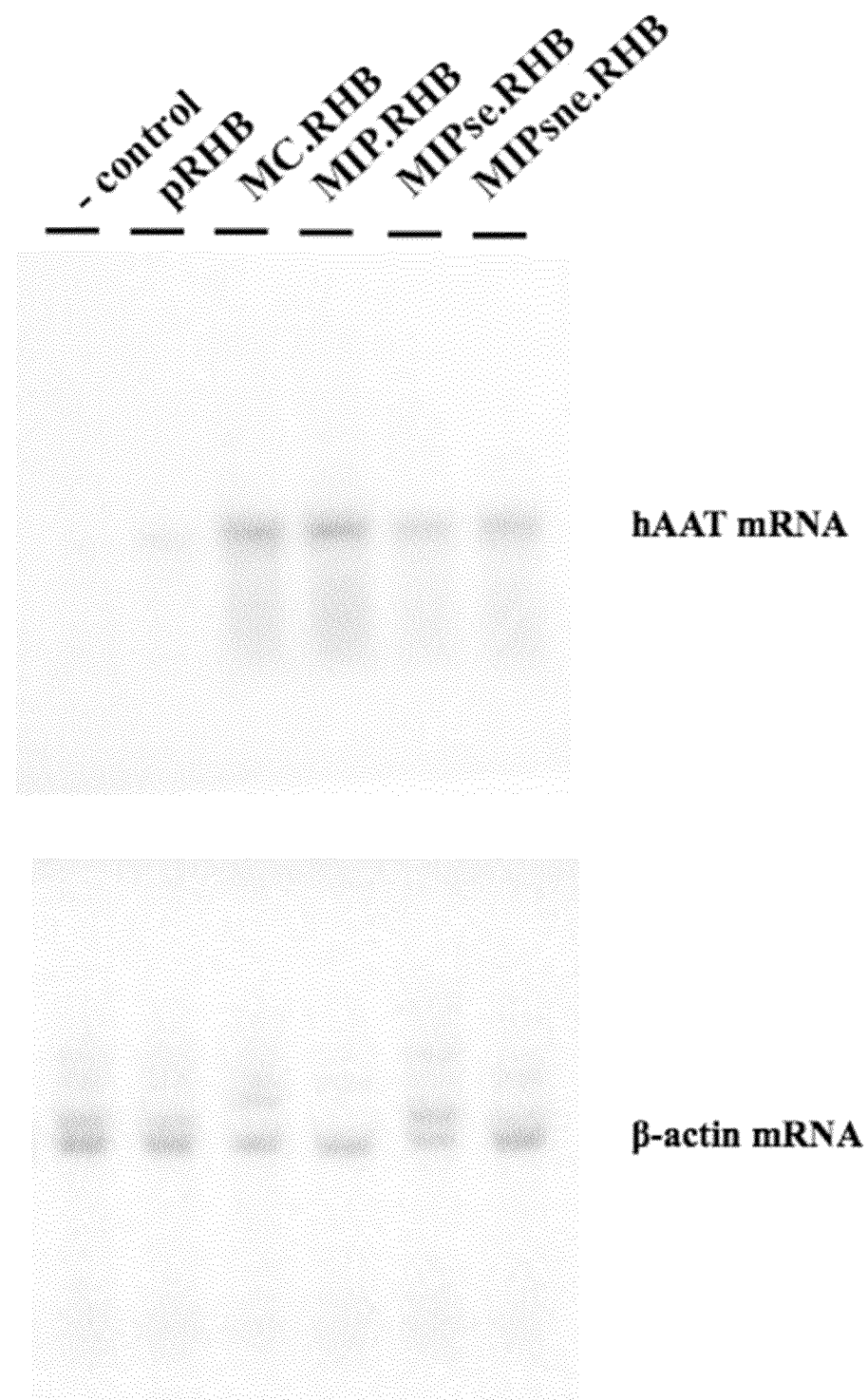
FIG. 8: Complete northern blot images for FIG. 1D.

In our previous studies (Chen et al., Minicircle DNA vectors devoid of bacterial DNA result in persistent and high-level transgene expression in vivo. *Mol Ther* 8, 495-500, (2003); Nakai et al., Extrachromosomal recombinant adeno-associated virus vector genomes are primarily responsible for stable liver transduction in vivo. *J Virol* 75, 6969-6976, (2001)), we demonstrated that the difference in transgene expression from plasmid and minicircle was not due to differential DNA loss. By quantitative PCR (qPCR) assay we were able to establish that the MIP vectors were maintained at the same level as minicircles and plasmids ranging from 1.8 to 2.5 copies per diploid genome 5 weeks after vector infusion (FIG. 1C). To establish if the engineered intron was correctly spliced out of the mRNA, we performed northern analysis (FIG. 1D, FIG. 8) 5 weeks after liver transfection. We found that all the MIP constructs produced one single-spliced product the same size as hAAT mRNA produced from pRHB and MC.RHB. This suggests that the presence of intron with PR sequence does not introduce alternative splicing. The strength of the northern blot signal from the use of the different vectors indicates that the difference in transgene expression was likely due to varied levels of transcription. These data establish that as we predicted, the MIP vectors provide persistent transgene expression via mechanisms similar to minicircle vectors (Lu et al., supra).

Figure 2A:
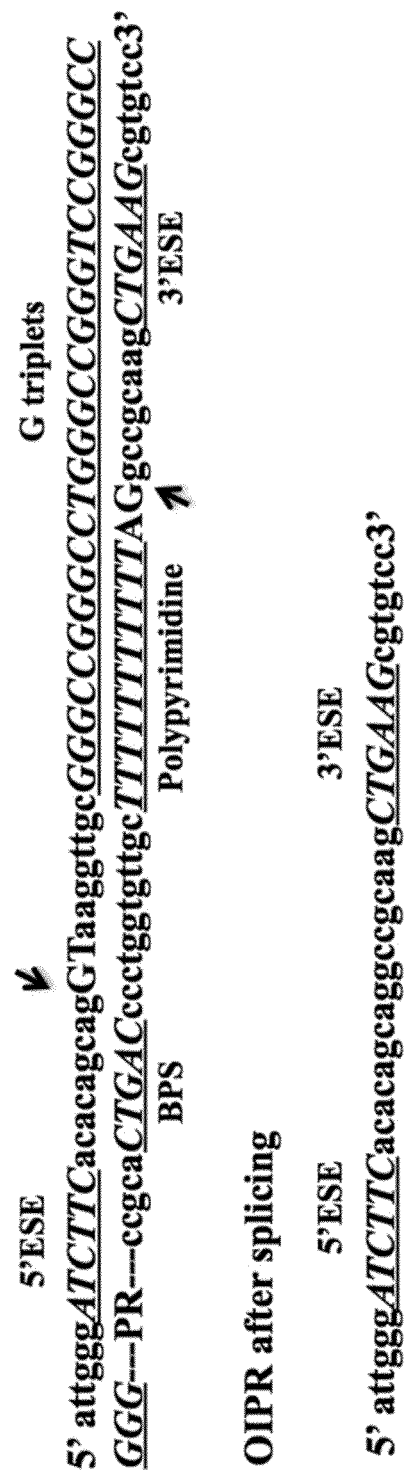
FIG. 2: RSV-hAAT expression constructs and transgene expression in mice. A(a) Structure and sequence of the optimized intron with a pUC origin and RNA-OUT sequence (OIPR) pre-splicing (flanking sequence 5' of PR, SEQ ID NO:1; flanking sequence 3' of PR, SEQ ID NO:2) and post-splicing (SEQ ID NO:33). 5' exon splicing enhancer (5'ESE), G triplets, branchpoint sequence (BPS), 11 nucleotide polypyrimidine track and 3' exon splicing enhancer (3'ESE) are underlined. Arrows indicate the sequence where splicing takes place. A(b) Schematics of DNA constructs containing the OIPR sequence. B) Equimolar amounts of DNA vectors shown in (Ab) were infused into C57BL/6J mice (n=5/group) and the serum hAAT determined at various time points (3 days, 1 week, 3 weeks, 5 weeks, 7 weeks and 9 weeks) after infusion. Error bars represent the standard deviation. C) Copy number of each construct per diploid genome in infused animal liver samples 63 days post-infusion via quantitative real time PCR. Two treated animals (light and dark gray) from each group were tested and each sample was performed in duplicate. Thus the mean value was determined by these four readings from each group. The mean value is indicated on each group. For pRHB, 1.3 (1.2 1.3, 1.3 and 1.3). For MC.RHB, 1.3 (1.3, 1.2, 1.4 and 1.4). For MIP.5'OIPR.RHB, 0.9 (0.9, 0.9, 1.0 and 0.9). For MIP.3'OIPR.RHB, 1.6 (1.6, 1.6, 1.6 and 1.6). For pMIP, 1.8 (1.9, 2.0, 2.0 and 1.4). D) Southern blot of 63 day post-infusion mouse liver genomic DNA samples (n=2/group). Genomic DNA samples were either single digested with BamHI (row 1), or double digested by BamHI and PmlI (row 2 and 3). The size of each vector is marked in bracket. Note that 3.3 kb, 3.5 kb and 5.0 kb bands are hard to distinguish on this Southern gel. 0, 5 and 20 copies of BamHI, PmlI double digested hAAT cDNA were loaded together with 20 μg non-infused negative control genomic DNA as copy number controls. Columns 1 and 2 were probed for hAAT and column 3 was probed for β-actin. E) Northern blot data. Two 63 day post-infusion liver total RNA samples from each group were subjected to northern blot. The hAAT and β-actin transcripts are indicated. A larger very faint was also detected in animals transfected with MIP.5'OIPR.RHB and MIP.3'OIPR.RHB vectors (black arrow heads). The bottom panel shows the over exposed northern blot. As indicated by white arrow heads, the same larger band was also detected in MC.RHB and pMIP.RHB infused groups. F) qPCR quantification of the reverse transcribed RNA-OUT or hAAT exonic regions (n=2/group). Primer details are in FIG. 9B and methods. The reverse transcription (RT) was performed on MC.RHB and MIP.5'OIPR.RHB infused groups by using RNA-OUT specific and hAAT specific primers. The cDNA products from RT reactions were further quantified through qPCR. G) Western blot of serum samples. 20 μl of 63 day post-infusion animal serum samples from each group (n=2/group) were analyzed. The 52 KDa protein bands corresponding to hAAT proteins are indicated. The 50 KDa protein marker band is indicated with an arrow. H) The yield of MIP vector and conventional plasmid vectors (n=4/vector). The mole/l yield was calculated as previously described (Kay et al., A robust system for production of minicircle DNA vectors. *Nat Biotechnol* 28, 1287-1289, (2010)). The linear TOPO2.1 vector (Invitrogen) was digested with EcoRI and then self-ligated to form TOPO2.1 empty vector. N=4 independent isolates.
Figure 2A:
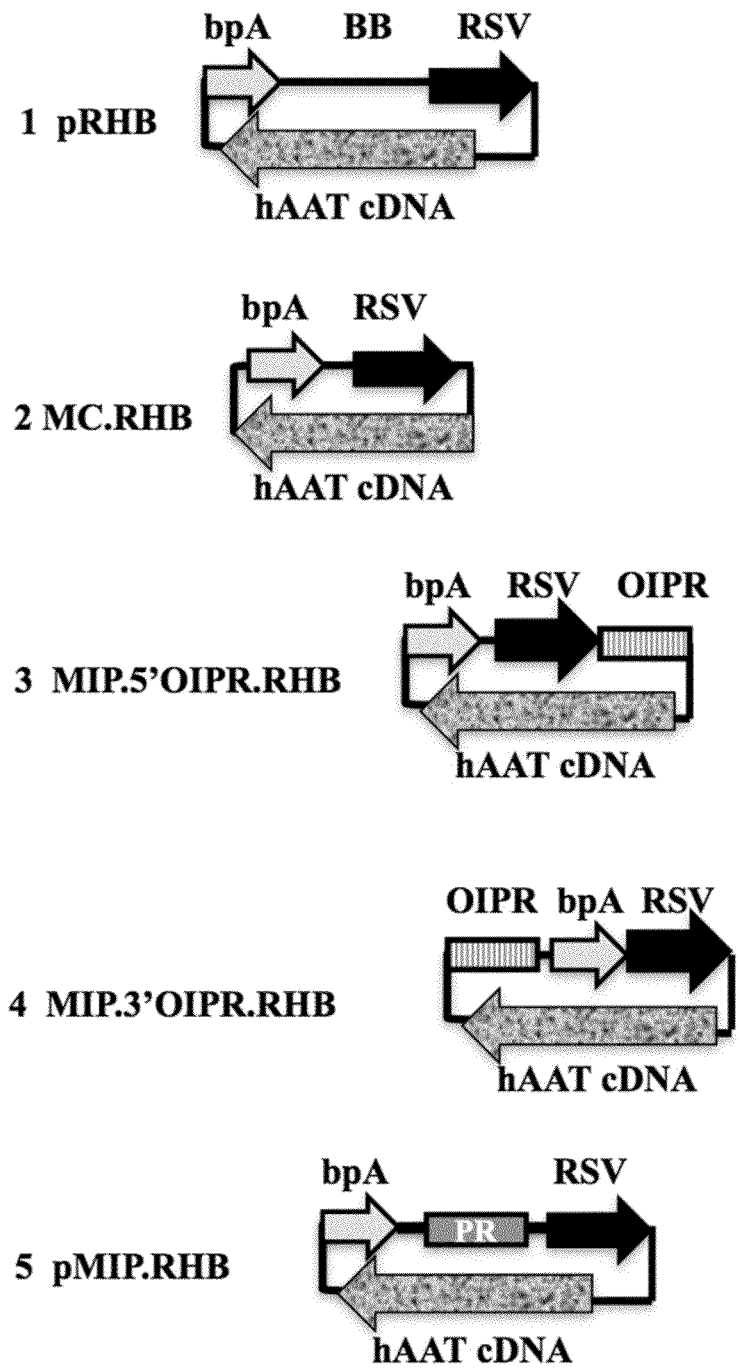
Figure 2B:
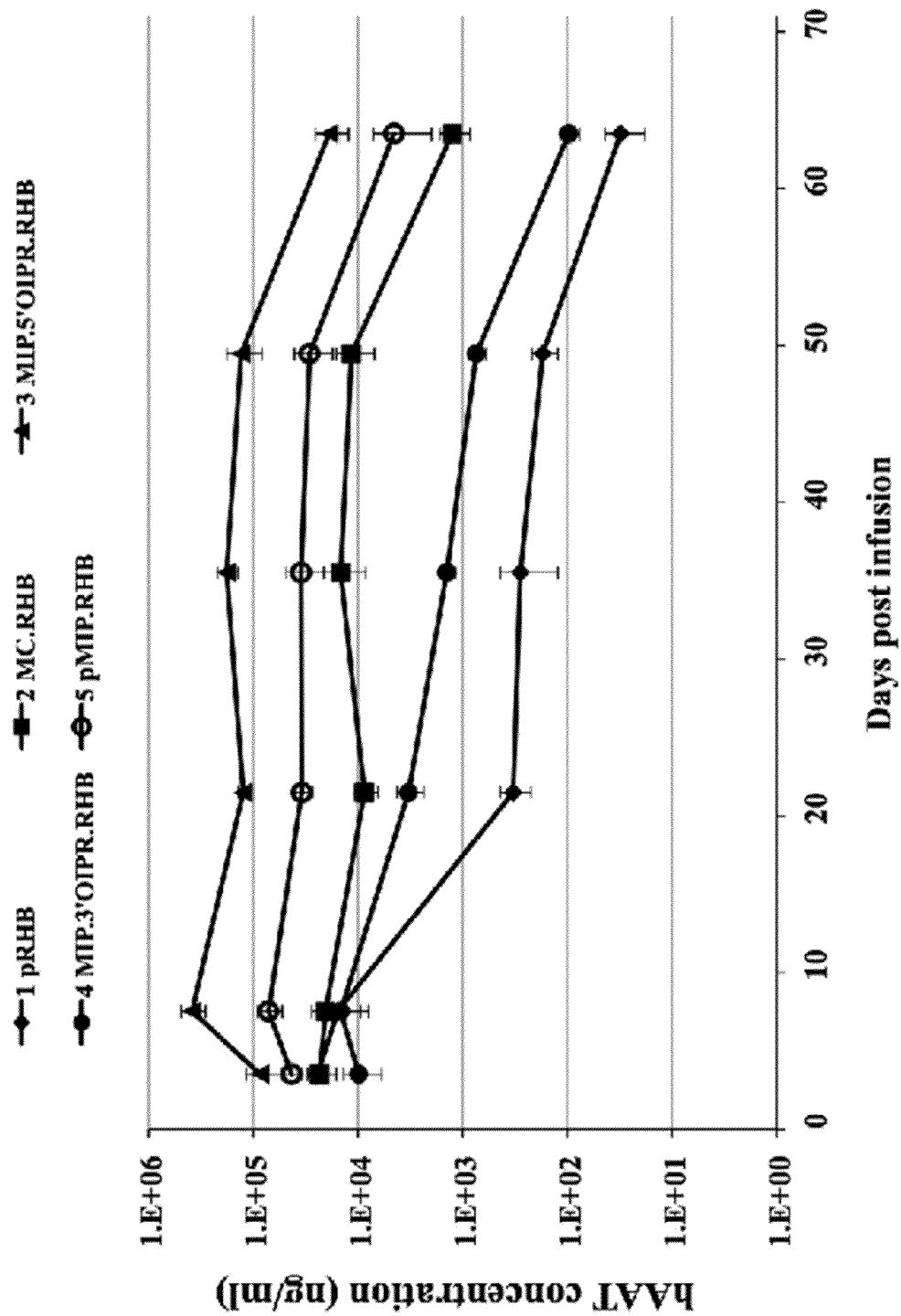
Figure 2C:
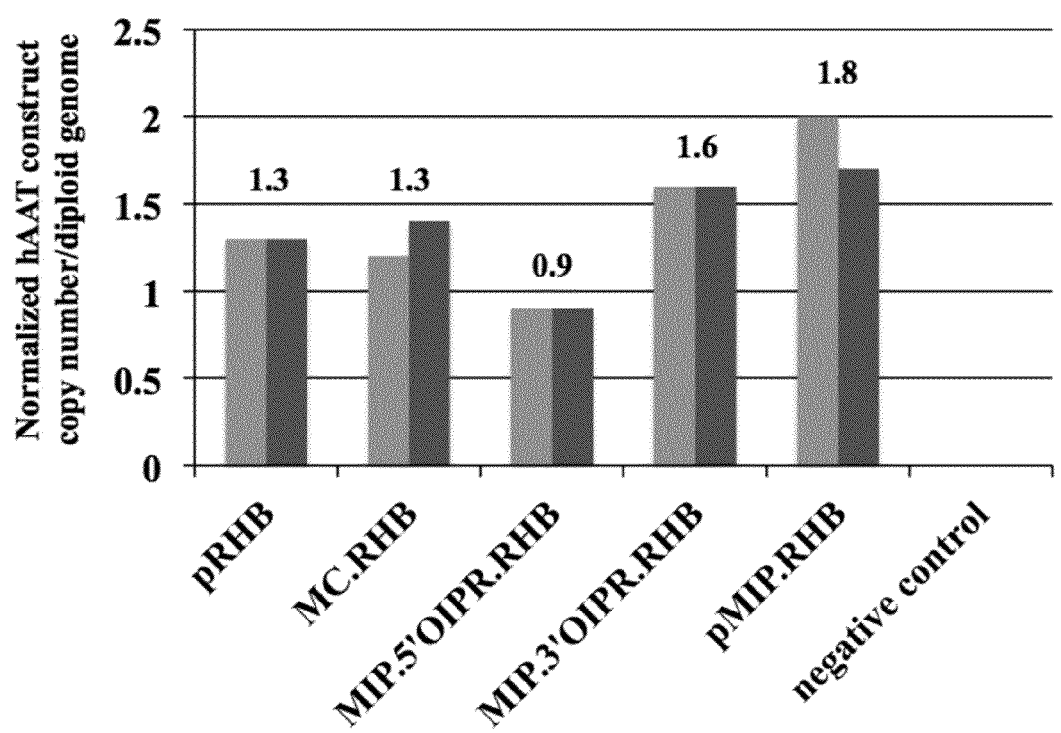
Figure 7B:
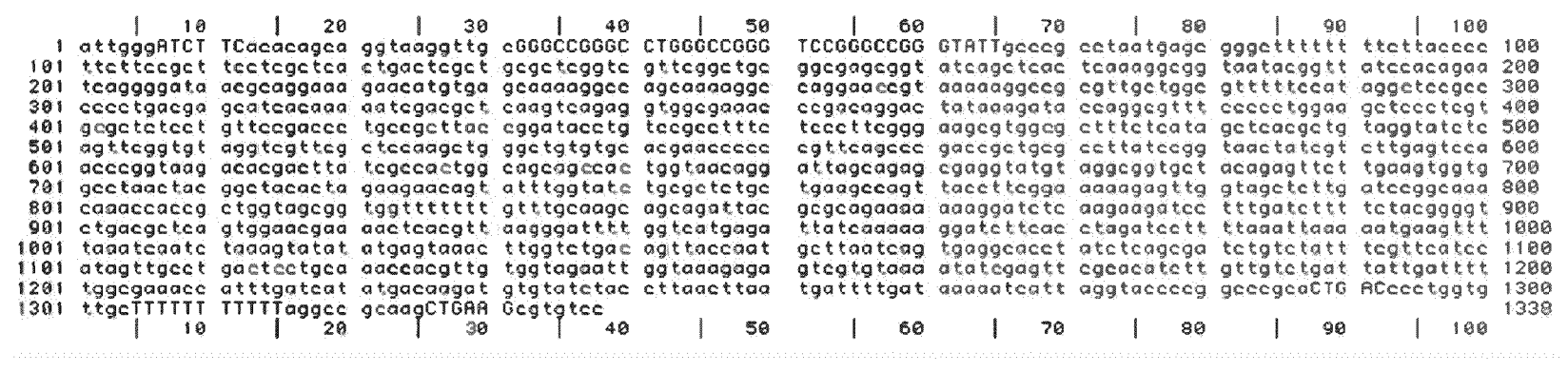

Optimized intronic sequences contained in a 5' non-coding exon provides sustained high levels of transgene expression in vivo. Having established proof-of-concept, we wanted to produce a MIP vector containing an intronic sequence that could be used with any expression sequence. To this end, vectors were designed that had an optimized intron with a pUC origin and RNA-OUT sequence (OIPR) placed within a 5' non-coding exon. The OIPR sequence contains the pUC origin and RNA-OUT sequence flanked by strong exonic splicing enhancers (Fairbrother et al., Predictive identification of exonic splicing enhancers in human genes. *Science* 297, 1007-1013, (2002)), G triplets (McCullough et al., G triplets located throughout a class of small vertebrate introns enforce intron borders and regulate splice site selection. *Mol Cell Biol* 17, 4562-4571 (1997)), a tract of 11 continuous polypyrimidines (Coolidge et al., Functional analysis of the polypyrimidine tract in pre-mRNA splicing. *Nucleic Acids Res* 25, 888-896, (1997)) and a consensus branch point sequence (FIG. 2Aa, FIG. 7B). To do this, the OIPR sequence was placed into a designated 5' non-coding exon (MIP.5'OIPR.RHB) or 3'UTR (MIP.3'OIPR.RHB) (FIG. 2A(b)). pRHB and MC.RHB vectors were used as silencing and non-silencing controls, respectively. A third control, plasmid pMIP.RHB, comprising the PR sequence (without splicing signals) replacing the conventional bacterial backbone, was constructed in order to determine if the presence of the PR sequence had any effect on transgene expression. This PR sequence is 1217 bp in length, bordering on the length known to cause silencing in previous studies (Lu et al., supra). However, it has also been previously reported that the presence of the RNA-OUT sequence in the plasmid backbone can enhance transgene expression (Luke et al., Improved antibiotic-free DNA vaccine vectors utilizing a novel RNA based plasmid selection system. *Vaccine* 27, 6454-6459, doi: 10.1016/j.vaccine.2009.06.017 (2009)).

All of the constructs were infused into mice. As demonstrated in FIG. 2B, the MIP.5'OIPR.RHB expressed the highest levels of transgene product even exceeding minicircle expression (MC.RHB) by ~15-times. Transgene expressed from pMIP.RHB followed the same kinetics as a minicircle vector and was 3-fold higher than MC.RHB, confirming that the PR sequence itself may improve transgene expression possibly serving a role as an enhancer. Comparing placement of the OIPR sequence as an intron into the 5' non-coding exon, MIP.5'OIPR.RHB increased transgene expression 4 to 5-fold higher than when the OIPR sequence was placed outside of the transgene expression cassette (pMIP.RHB), suggesting that RNA splicing of transcripts derived from MIP.5'OIPR.RHB enhanced expression and/or partial transcriptional silencing of the pMIP.RHB plasmid were contributory. When the OIPR sequence was made as part of the 3'UTR (MIP.3'OIPR.RHB), the transgene expression was not enhanced, probably because changes in the 3'UTR can affect mRNA stability. Therefore, we abandoned the idea of trying to place the intronic sequences into the 3'UTR.

Figure 2D:
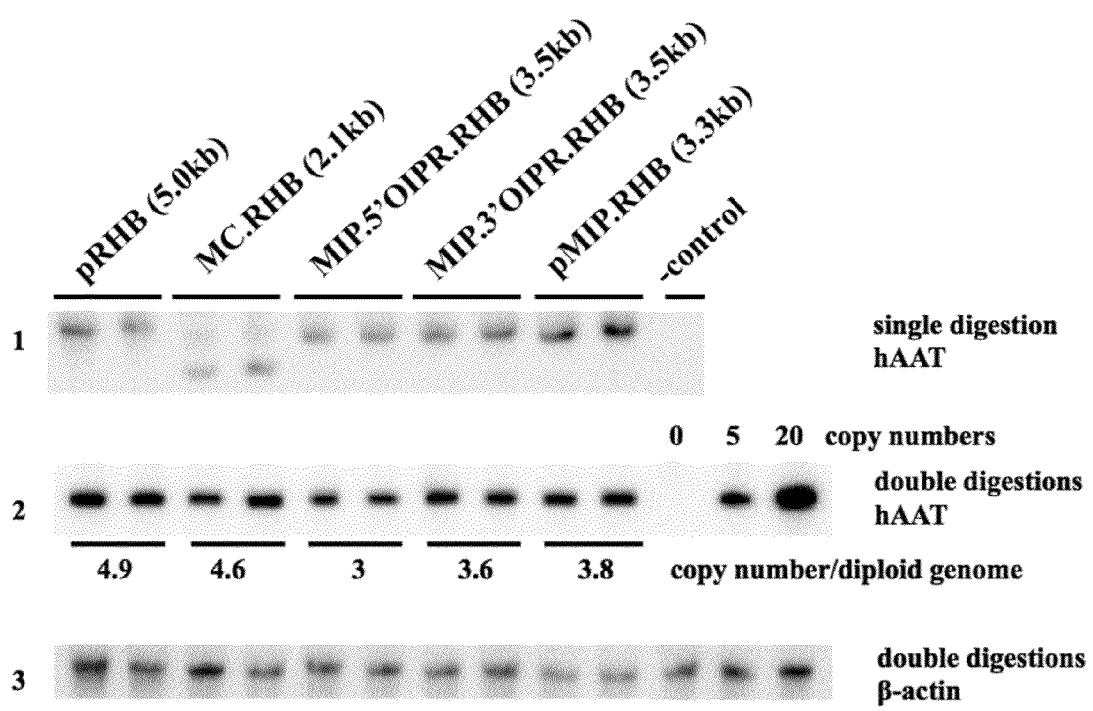

To verify that the high level of transgene expression from MIP.5'OIPR.RHB was not due to differential loss or maintenance of episomal DNA vectors, we performed both quantitative PCR (qPCR) assays (FIG. 2C) and Southern blot analysis (FIG. 2D) of the livers of treated animals nine weeks after vector infusion. Single restriction enzyme digestion that cut each vector once verified that the infused vectors remained episomal. The vector copy number per diploid genome varied by two-fold or less between all groups as determined in both qPCR (FIG. 2C) and Southern blot (FIG. 2D) assays.

Figure 2E:
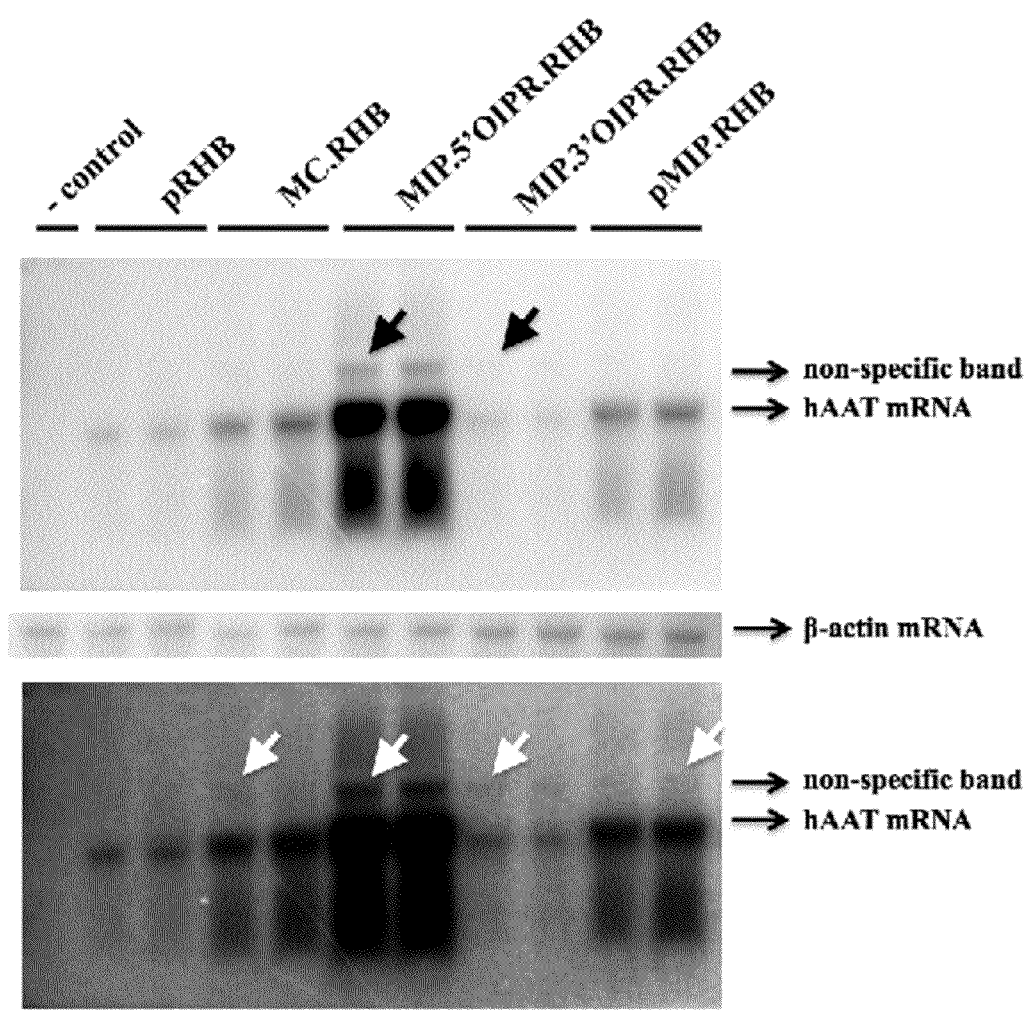
Figure 2F:
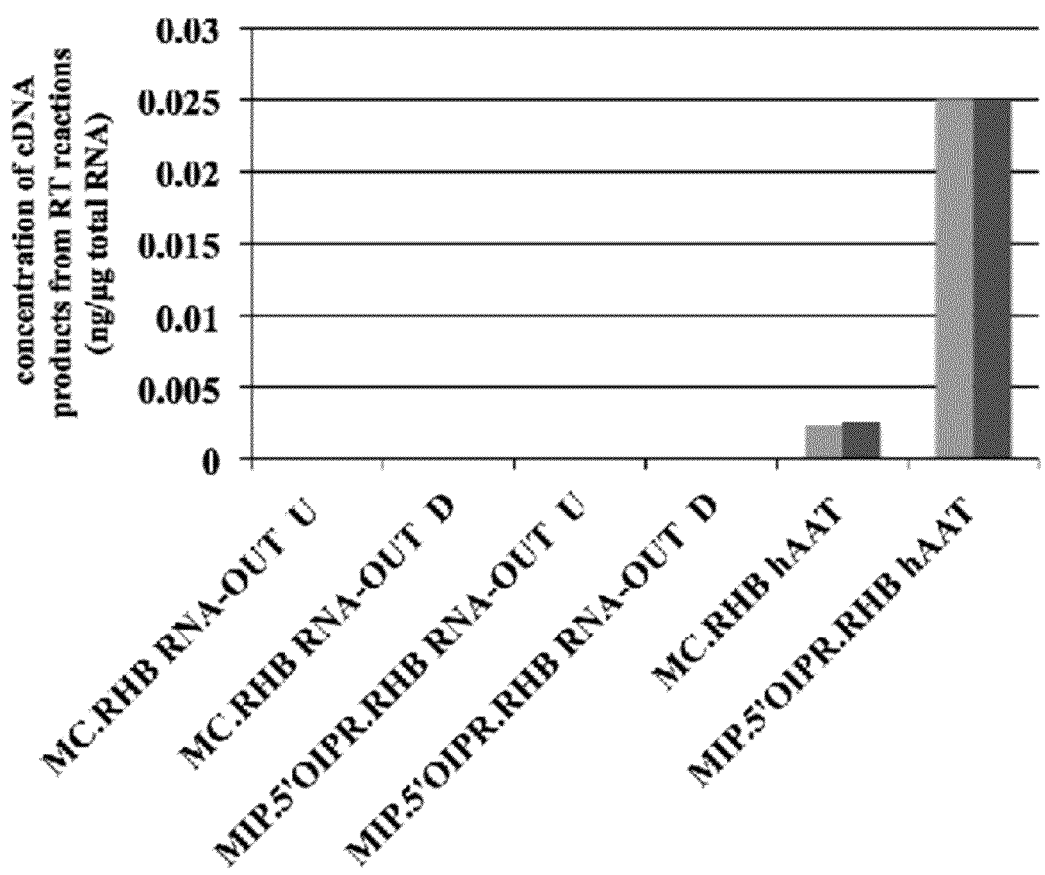
Figure 9A:
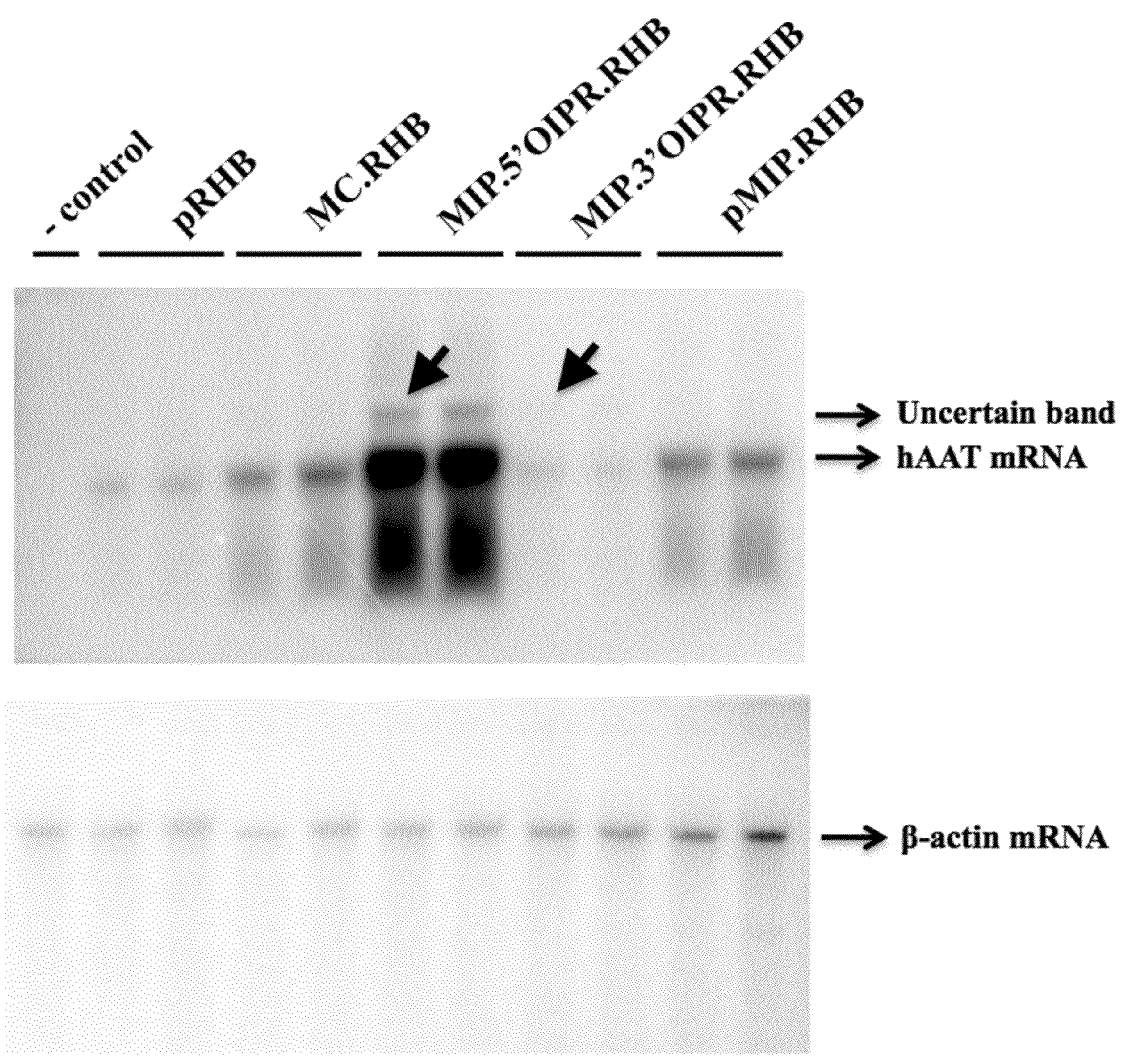
FIG. 9: Complete northern blot images and description of the RNA-OUT primers used for RT and qPCR reactions. A) Complete northern blot images for FIG. 2E. B) Schematic diagram for the RNA-OUT primers. RNA-OUT U and RNA-OUT D were used for RT reactions. RNA-OUT qPCR U and RNA-OUT qPCR D are the nesting oligos that were used to further amplify RNA-OUT sequence through qPCR reactions. C) The primers in B were tested for their abilities to amplify the RNA-OUT sequence from MIP.5'OIPR.RHB DNA template. RNA-OUT U and RNA-OUT D were able to amplify 145 bp RNA-OUT fragment and RNA-OUT qPCR U and RNA-OUT qPCR D were able to amplify 127 bp RNA-OUT fragment (black arrow heads).
Figure 9B:
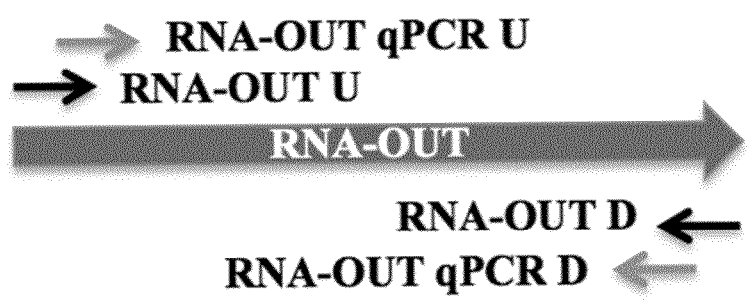
Figure 9C:
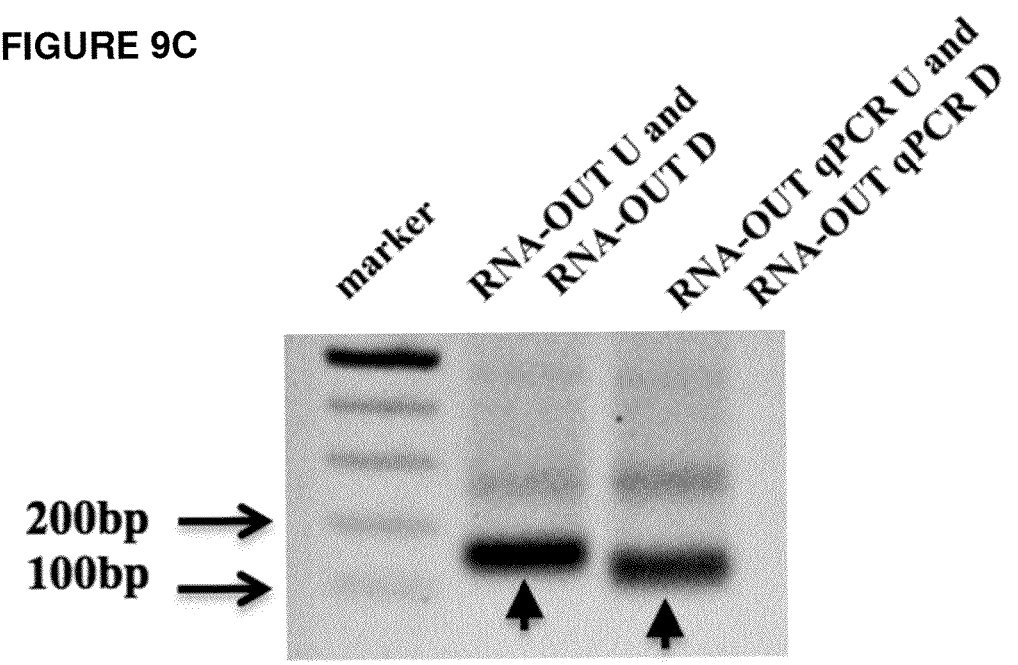

To determine the splicing patterns of all tested constructs and to verify if the different levels of transgene product and mRNAs were correlative, northern blot analyses were performed. As shown in FIG. 2E and FIG. 9A, the hAAT transcript levels correlated with the level of protein expression with the MIP.5'OIPR.RHB infused group having the highest amount of transcript. A trace amount of a larger sized band was detected in the MIP.5'OIPR.RHB and MIP.3'OIPR.RHB infused groups. However, the same sized band was detected in MC.RHB and pMIP.RHB infused samples when the blot was exposed for longer periods (FIG. 2E, bottom panel), suggesting that this band most likely represented a non-specific signal and was not the result of an unspliced or mis-spliced mRNA. To prove this point, a series of reverse transcription (RT) and qPCR experiments were performed using various primers derived from exonic hAAT flanking and/or RNA-OUT intronic sequences. The presence of exon-exon but not intronic amplification products shown in FIG. 2F and FIG. 9B confirmed the absence of an unspliced mRNA. Consistent with this finding was the fact that no protein isoforms were detected by Western blot analyses performed on serum from transfected mice (FIG. 2G) or transfected cell lysate samples (FIG. 3C).

Figures 2G, 2H:
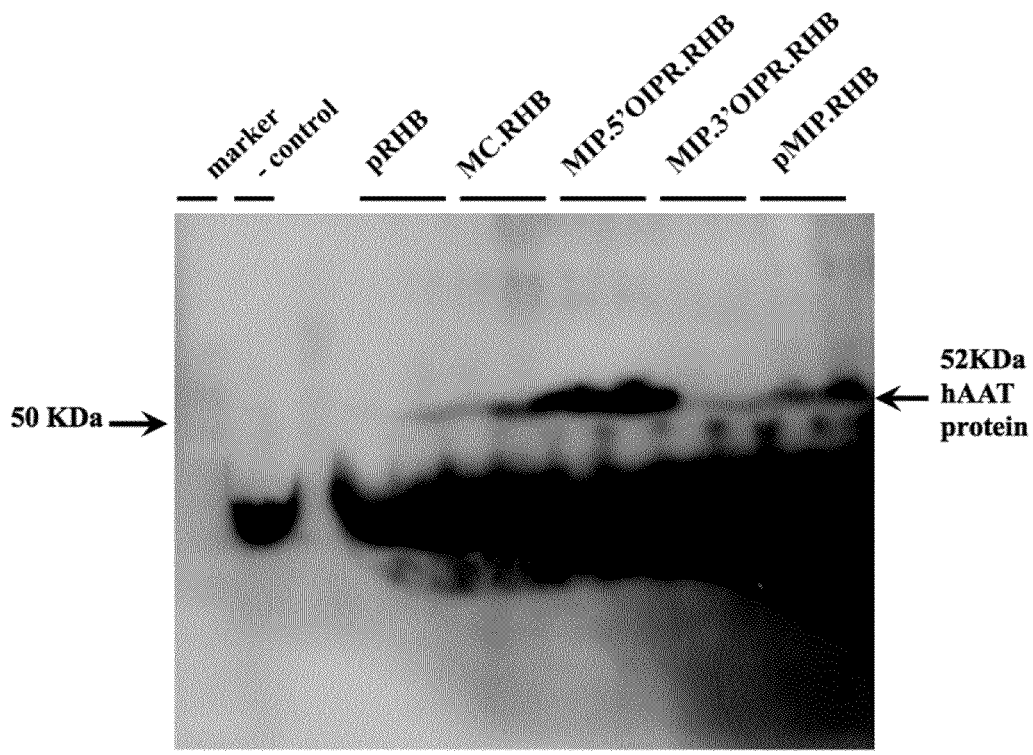

The yield of mip vectors is similar to canonical plasmids. The amount of MIP vectors produced in routine bacterial cultures was compared with routine plasmids. Two MIP vectors and two bacterial plasmids were propagated and purified from 100 ml cultures 4 times each (FIG. 2H). The yield of MIP was at least as high as that obtained with the conventional plasmids.

The presence of pr sequence in the 5' non-coding exon expressed the highest levels of transgene in vivo comparing with conventional plasmid and minicircle vectors.

Figure 3A:
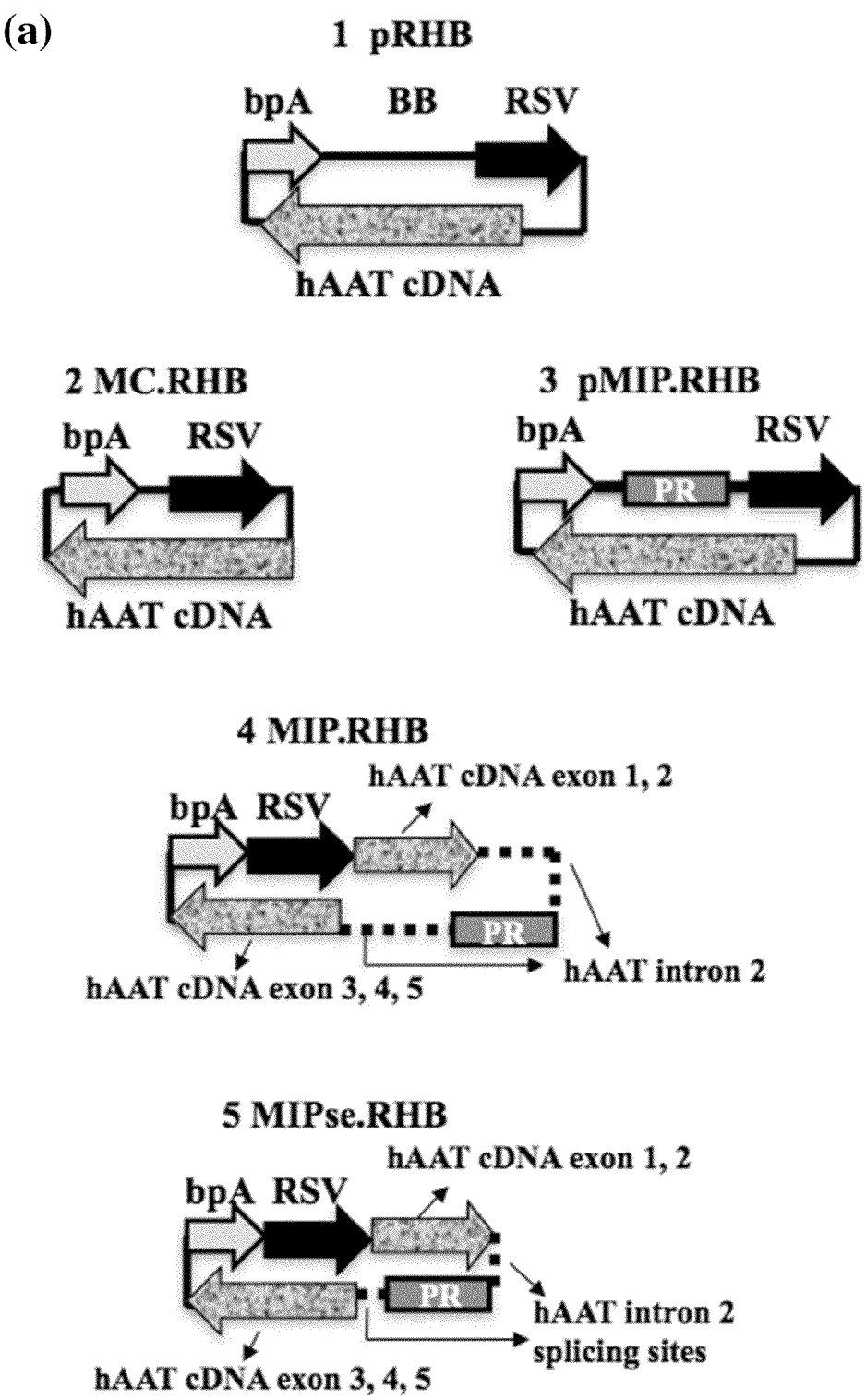
FIG. 3: RSV-hAAT expression constructs and transgene expression in mice. A(a) Schematic of hAAT expressing DNA constructs. A(b) Structure of optimized intron 2, comprising intron 2 flanked by optimized 5' exon splicing site (SEQ ID NO:3) and 3' exon splicing site (SEQ ID NO:4). Arrows indicate the sequence where splicing takes place. B) Equimolar amounts of DNA vectors shown in FIG. 3A(a) were infused into mice (n=5/group). The serum hAAT were determined at various time points (1 week, 3 weeks, 5 weeks, 7 weeks, and 13 weeks) after infusion. Error bars represent the standard deviation. C) Western blot from HEK293 cell lysates. transfected with DNA constructs listed in FIG. 3Aa 24 hours earlier. The 52 KDa hAAT protein bands are indicated. The smaller sized bands likely reflect degraded proteins. The 50 KDa protein marker band is indicated with an arrow.
Figure 3A:
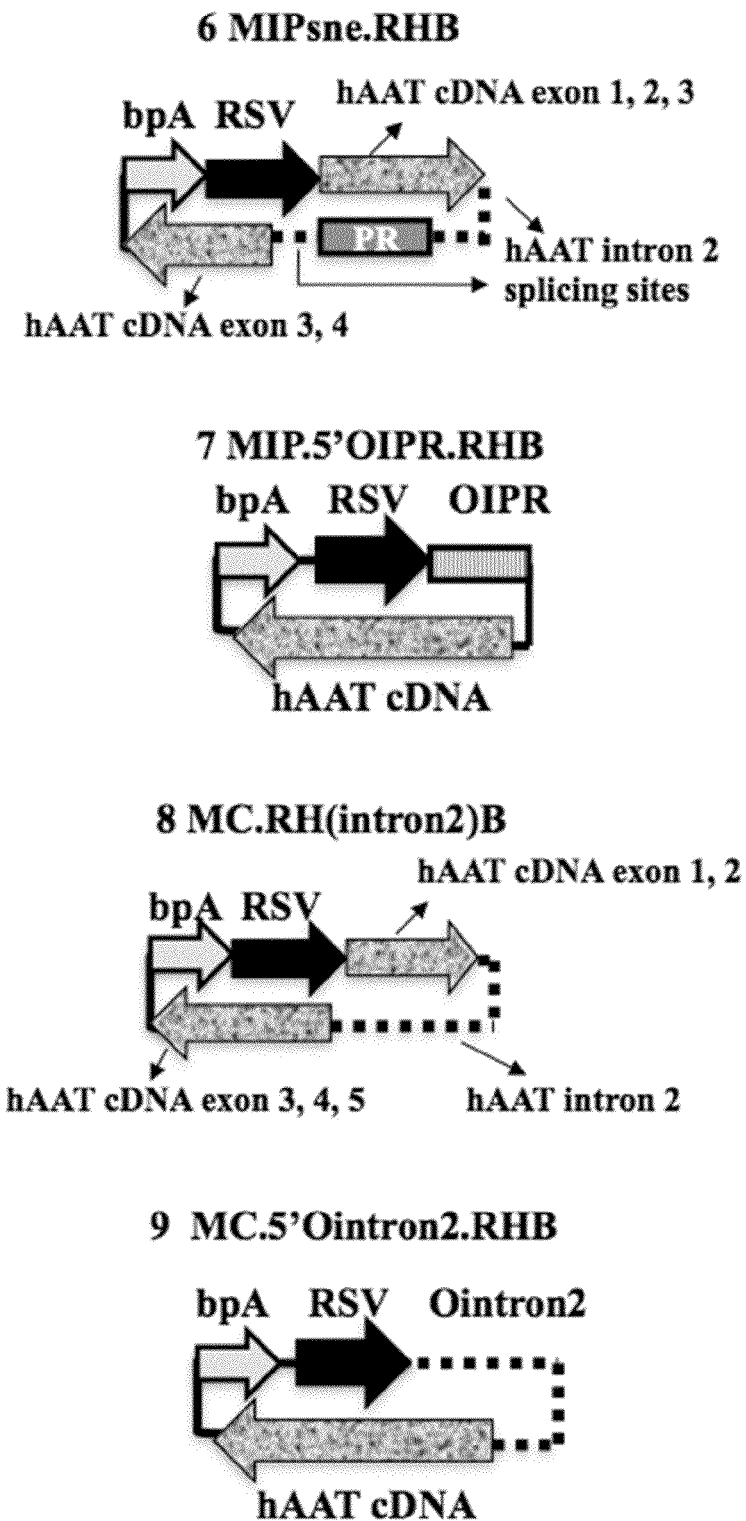
Figure 3A:

To establish whether the high level of transgene expression from MIP.5'OIPR.RHB vector was due to the presence of the PR sequence itself, an experiment using additional control vectors were tested for transgene expression (FIGS. 3A and 3B). A minicircle vector containing an hAAT intron 2 at the endogenous location without the PR sequence ("MC.RH(intron2)B") and a minicircle vector containing the hAAT intron2 in the 5' non-coding exon flanked by the 5' exon splicing enhancer (5'ESE) and 3' exon splicing enhancer (3'ESE) ("MC.5'Ointron2.RHB") were constructed (FIG. 3A(a); Ointron2 sequence of MC.5'Ointron2.RHB diagrammed in FIG. 3A(b)). As shown in FIG. 3B, during this 3-month experiment, the MIP.5'OIPR.RHB treated mice expressed the transgene at about 7-fold higher levels than the MC.5'Ointron2.RHB treated mice, and resulted in about 10-times higher levels of transgene expression compared to the corresponding minicircle MC.RHB. Western blot analysis confirmed that the protein produced from these vectors was a single isoform (FIG. 3C). These data indicate that the PR sequence contributes to high level expression, and that to achieve highest expression, both the placement and sequence of the selectable marker should be considered.

Figure 4A:
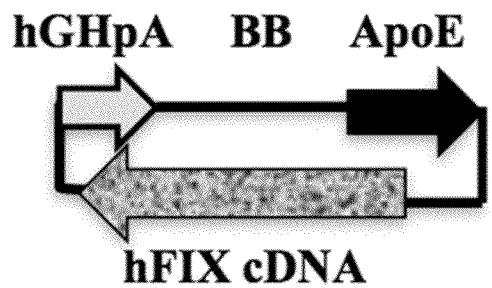
FIG. 4: ApoE.hFIX expression constructs and transgene expression in mice A) Schematic of hFIX expressing DNA constructs. B) The same molar amounts of DNA constructs shown in A were injected into mice (n=5/group) and the plasma hFIX levels were measured by ELISA at various time points (3 days, 1 week, 3 weeks, 5 weeks, 7 weeks, 9 weeks, and about 30 weeks) after injection. Error bars represent the standard deviation. C) Structure of the universal MIP cloning vector.
Figure 4A:
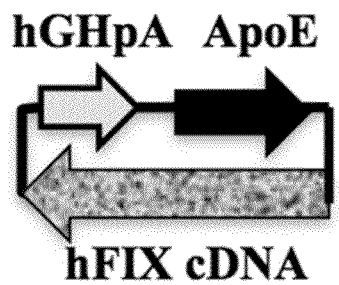
Figure 4A:
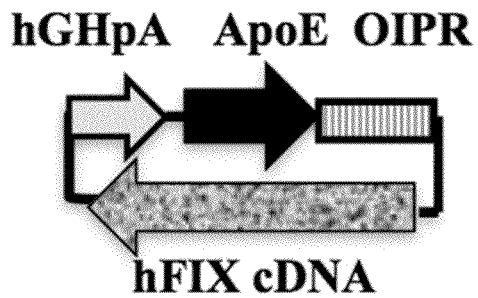
Figure 4B:
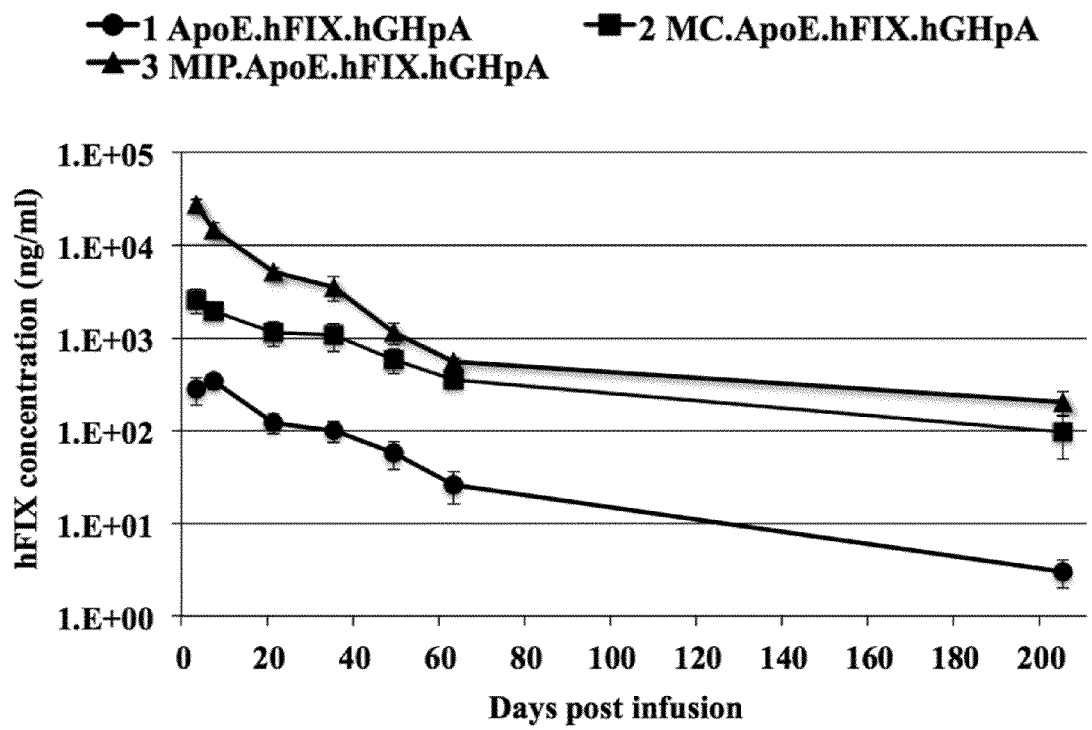
Figure 10A:
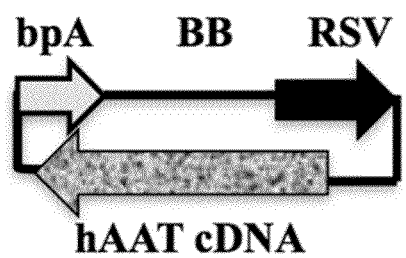
FIG. 10: RSV.hAAT expression constructs and transgene expression in mice. A) Schematic of hAAT expressing DNA constructs. B) The same molar amounts of DNA constructs shown in A were injected into mice (n=5/group) and the serum hAAT levels were measured by ELISA at various time points. Error bars represent the standard deviation.
Figure 10A:
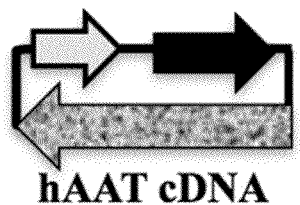
Figure 10A:
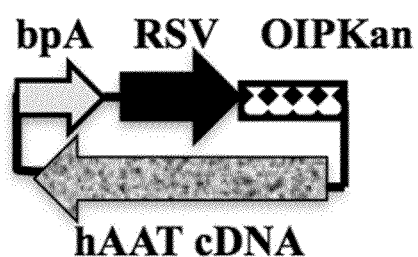
Figure 10B:
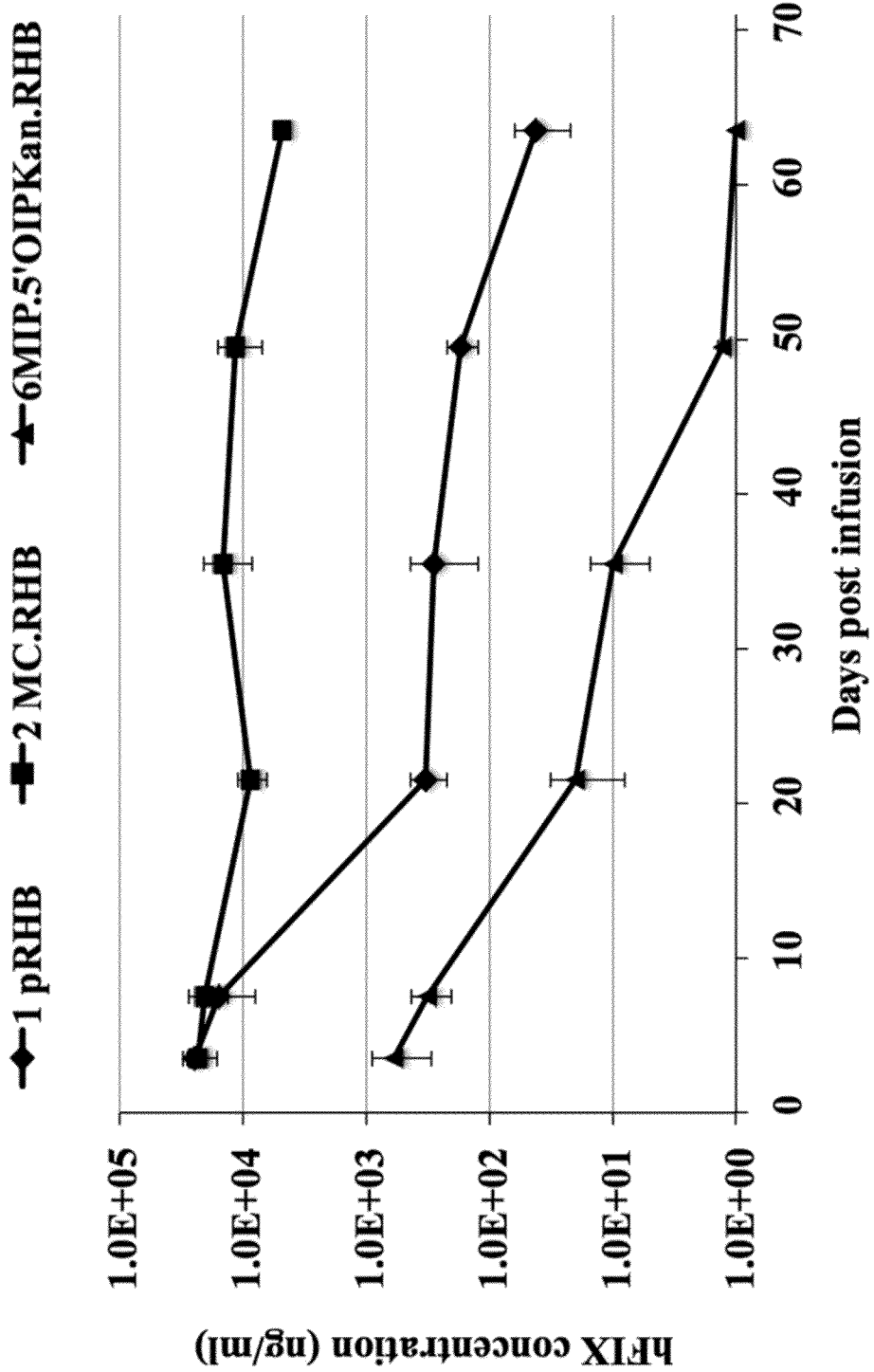

To establish the utility of these vectors, we constructed an MIP vector using a different promoter and transgene. Sustained high levels of human factor IX (hFIX) driven by the ApoE.HCR.hAAT promoter (Miao et al., Inclusion of the hepatic locus control region, an intron, and untranslated region increases and stabilizes hepatic factor IX gene expression in vivo but not in vitro. *Mol Ther* 1, 522-532, (2000)) were achieved in transfected mice (FIGS. 4A and 4B). The MIP.ApoE.hFIX.hGHpA treated mice had two-times higher levels of transgene expression compared to the corresponding minicircle (MC.ApoE.hFIX.hGHpA) treated animals 7-months after infusion User-friendly improvements in Parental MIP Design. Antibiotic selection is more commonly used in plasmid DNA propagation so we attempted to replace the RNA-OUT selectable marker in the OIPR sequence with the more commonly used kanamycin resistance gene (FIG. 10A). However, transgene expression was almost two orders of magnitude lower even at the early time points compared to a routine plasmid (FIG. 10B). This was not surprising because these sequences provide potential alternative splicing sites. Because similar sites exist in other antibiotic selectable markers, we continued to exclusively pursue the RNA-OUT selectable marker in the MIP vector for plasmid propagation.

Figure 4C:
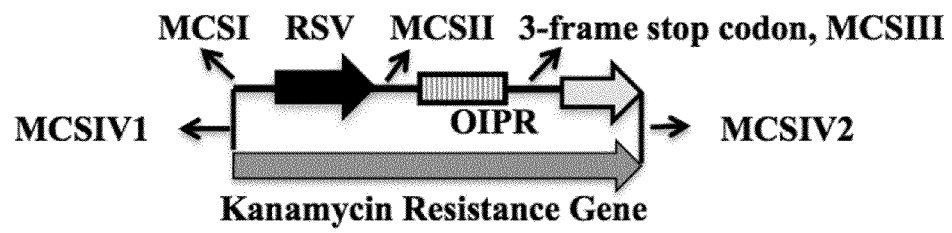

To make an MIP vector suited for routine cloning of any expression cassette, we constructed a universal MIP cloning vector (MIP Parental Vector) containing the OIPR site, RSV promoter and bpA polyA signal flanked by multiple cloning sites (MCS) (FIG. 4C). In this vector MCSI and MCSII can be used to replace the RSV promoter with any other promoter and any transgene coding sequence can be inserted into MCSIII region. In the small chance of producing unspliced or mis-spliced mRNA, we cloned a 3-frame stop codon (TGAC-TAGCTAA) into MIP parental vector between the 3'end of OIPR sequence and the 5'end of MCSIII.

While cloning various expression cassettes into the MIP vector, we found that the growth of non-transfected host bacteria on sucrose selection plates increased the number of false positive clones. To make the cloning step more efficient, we incorporated a kanamycin resistance gene in the backbone between MCSIV1 and MCSIV2 restriction sites. This allowed Kanamycin selection for the purposes of cloning. The kanamycin gene was then simply removed by a single enzyme restriction digest of the MCSIV1 and MCSIV2 sites followed by self ligation to produce the final MIP vector. The vectors derived by this method are stable and easily propagated using RNA-OUT selection.

Figure 5A:
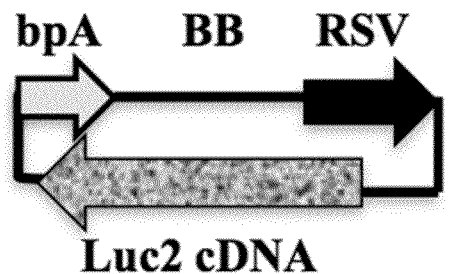
FIG. 5: RSV.Luc2 expression constructs and transgene expression in mice and in HEK293 cells. A) Schematic of firefly luciferase2 expressing DNA constructs. B) The same molar amounts of DNA constructs shown in A were injected into 6-8 week FVB mice (n=5/group) and the in vivo liver firefly luciferase2 expression levels were measured at day 1 after infusion. The animals were exposed for 1 second. Average Radiance (average photons) of each image was marked under the image. C) DNA vectors in A were transfected into HEK293 cells with the renilla luciferase control vector pRL-SV40 at the ratio of 50:1 (n=3 for each group). Firefly luciferase2 and renilla luciferase signals were analyzed by VERITAS microplate luminometer at 24 hours after transfection. The firefly luciferase2 signals were normalized to the renilla luciferase signal.
Figure 5A:
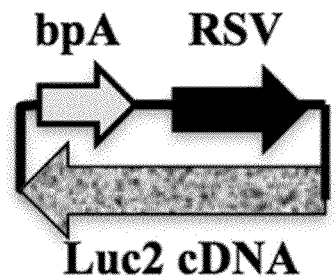
Figure 5A:
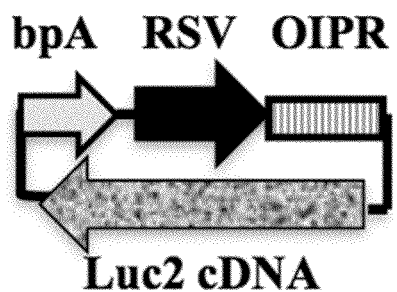
Figure 5B:
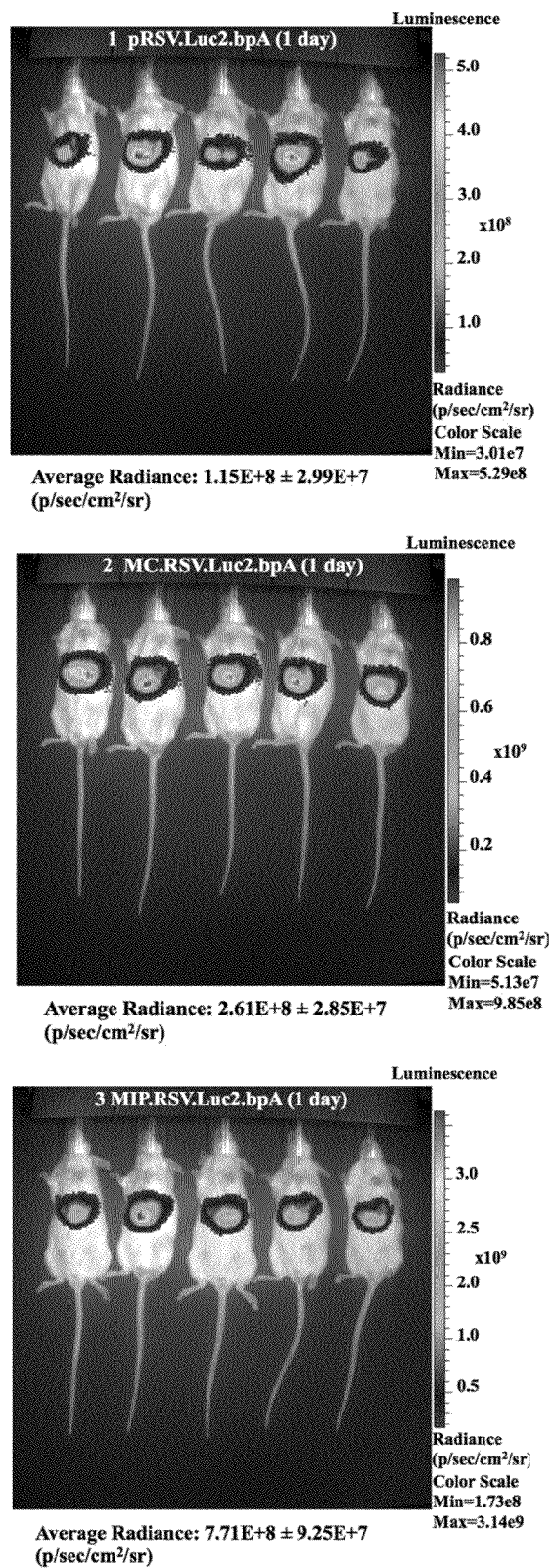

MIP vectors produce functional protein products and provide higher levels of transgene expression compared to canonical plasmids in vivo and in vitro. While the secreted proteins produced by MIP were of the expected size, we wanted to test a third transgene product and unequivocally establish the production of a functional protein. To do this, the firefly luciferase2 gene was cloned into MIP parental vector (MIP.RSV.Luc2.bpA) (FIG. 5A). Vectors pRSV.Luc2.bpA and MC.RSV.Luc2.bpA were used as plasmid and minicircle controls. The same molar amount of these three vectors was infused into the livers of 6-8 week-old FVB female mice by hydrodynamic tail vein injection. Since firefly luciferase may induce an anti-luciferase immune response (Jeon et al., Immune response to firefly luciferase as a naked DNA. *Cancer biology & therapy* 6, 781-786 (2007); Wilber et al., Dynamic gene expression after systemic delivery of plasmid DNA as determined by in vivo bioluminescence imaging. *Human gene therapy* 16, 1325-1332 (2005); Limberis et al., Identification of the murine firefly luciferase-specific CD8 T-cell epitopes. *Gene therapy* 16, 441-447 (2009)) we measured the firefly luciferase2 expression 1 day and 3 days after infusion. As shown in FIG. 5B, expression of firefly luciferase2 from an expression cassette on the MIP vector was 3-fold and 7-fold higher, respectively, than expression from the same expression cassette on a conventional minicircle or conventional plasmid vector one day after infusion. Three days after infusion, luciferase2 expression from the MIP vector were still elevated relative to the level of luciferase2 expressed from the minicircle or plasmid vector.

Figure 5C:
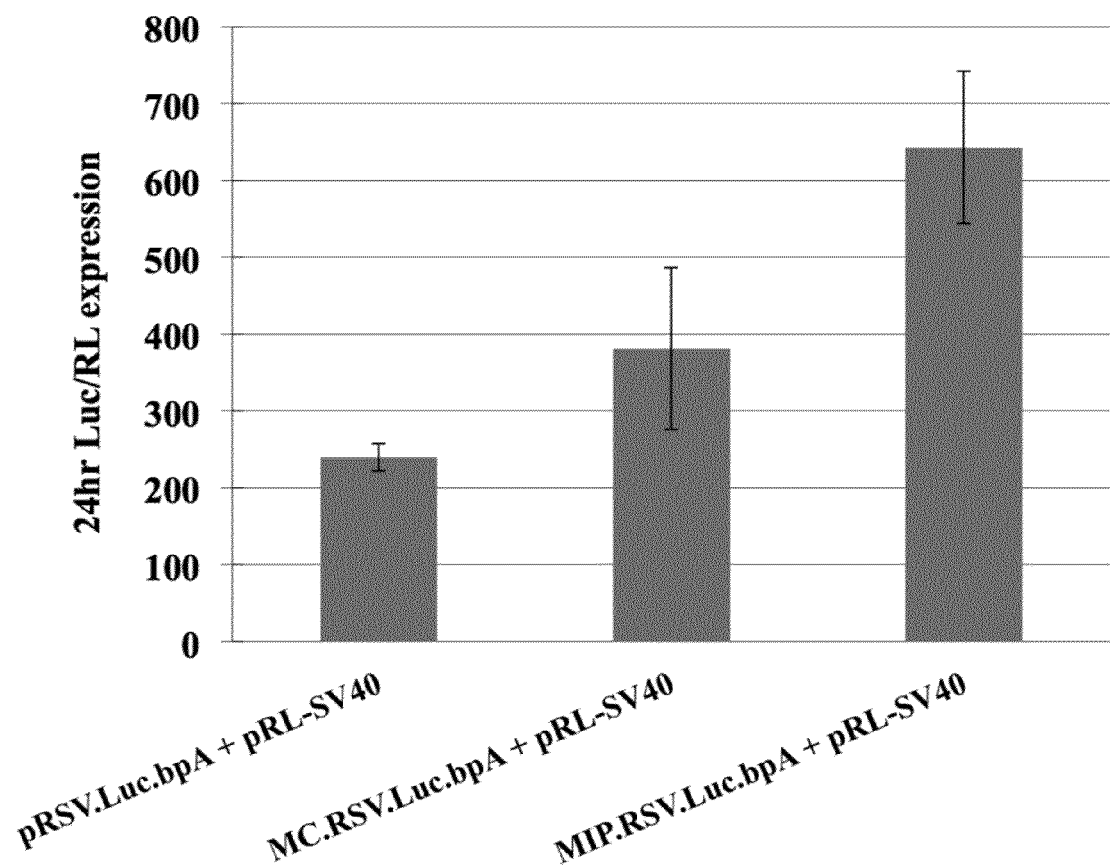
Figure 6A:
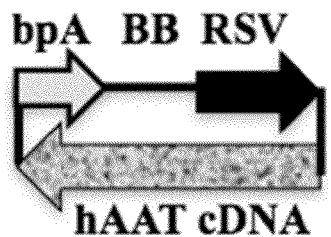
FIG. 6: Transgene expression levels in HEK293 cells, normalized to plasmid-expressed GFP. A) Schematic of hAAT expressing DNA constructs and GFP construct that used for HEK 293 transfection. B) hAAT levels in the culture media were quantified every 24 hours at 24 hours, 48 hours and 72 hours after transfection by ELISA (n=5/group). The hAAT levels are presented as pg/plated cell/24 hr.
Figure 6A:
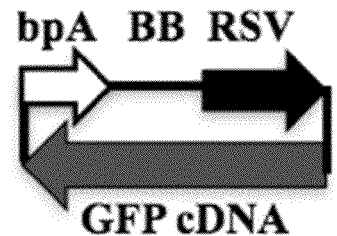
Figure 6A:
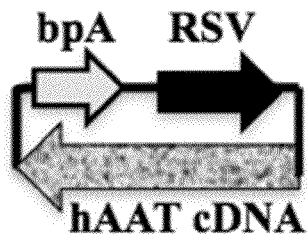
Figure 6A:
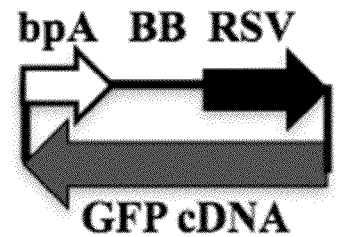
Figure 6A:
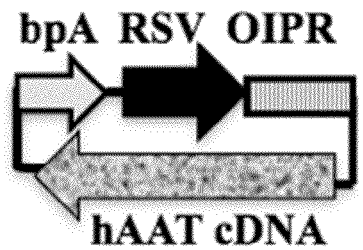
Figure 6A:
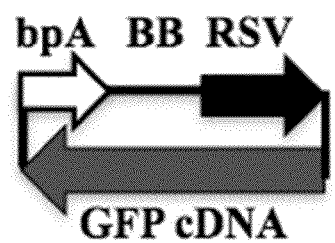
Figure 6A:
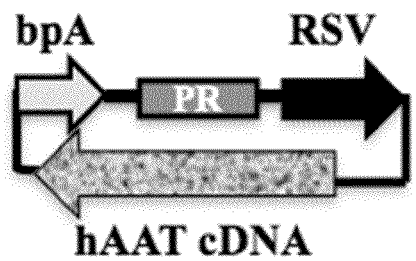
Figure 6A:
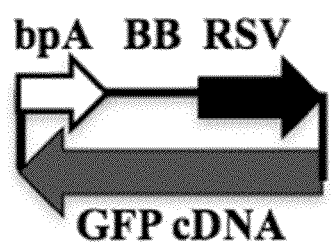
Figure 6B:
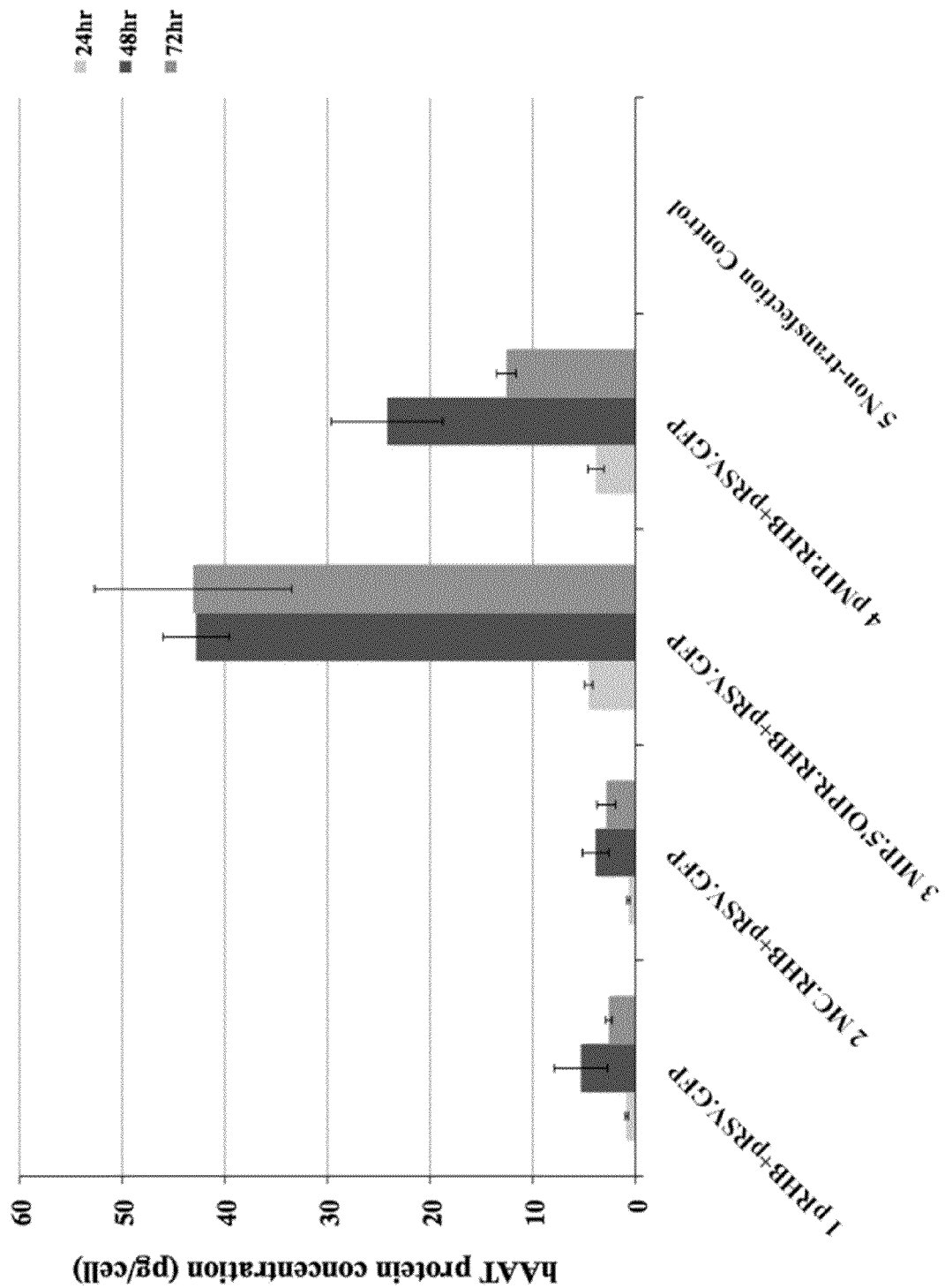
Figure 11:
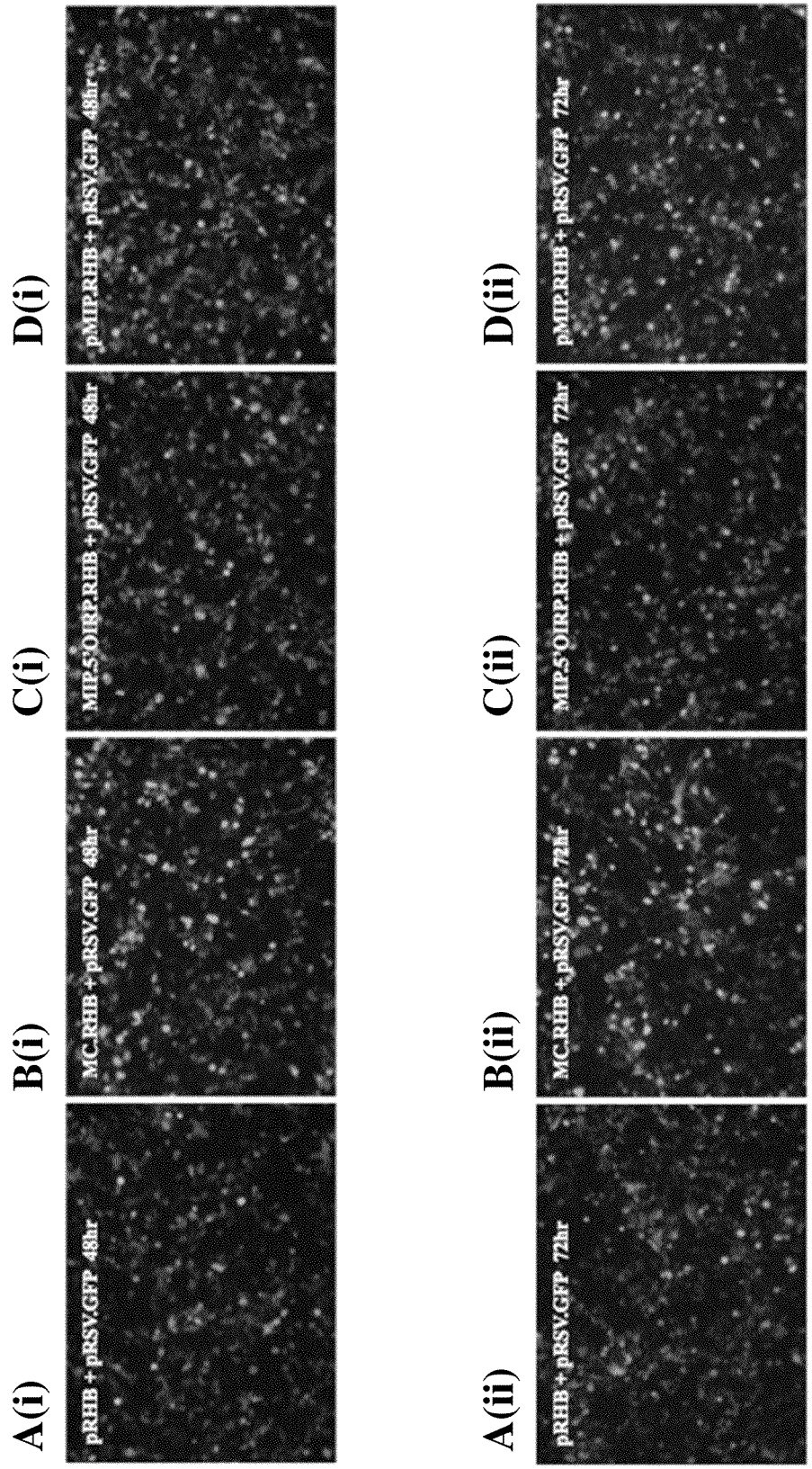
FIG. 11: GFP expression as transfection efficiency control. The same molar amount of various plasmid, minicircle, or MIP vector DNA was co-transfected with pRSV.GFP construct (molar number of vector:molar number of pRSV.GFP construct=3:1) into HEK293 cells with the same confluence. GFP expression was checked 24 hours, 48 hours and 72 hours after transfection. A) pRHB+pRSV.GFP. B) MC.RHB+pRSV.GFP. C) MIP.5'OIPR.RHB+pRSV.GFP. D) pMIP.RHB+pRSV.GFP. i) 48 hours after transfection. ii) 72 hours after transfection. GFP expression 24 hours after transfection not shown, due to low level of expression. Non-transfection controls also not shown, due to no expression observed.

We wanted to compare the relative differences in transgene expression in cultured cells. To do this we used the same molar amount of pRSV.Luc2.bpA, MC.Luc2.bpA and MIP.RSV.Luc2.bpA and $\frac{1}{50}^{th}$ the molar amount of a renilla luciferase expression plasmid, pRL-SV40 (Promega), were transfected into human HEK293 cells. The firefly luciferase2 expression levels were normalized for renilla luciferase. As shown in FIG. 5C, MIP vector expressed firefly luciferase2 at about 2.5, and 6-times higher levels than a minicircle and conventional plasmid vectors, respectively 72 hours after transfection. A similar experiment was performed using the hAAT expression vectors. The same molar amount of plasmid, minicircle and MIP vectors expressing hAAT (FIGS. 6A and 6B) and a GFP transfection control plasmid (FIG. 11) were transfected into human HEK293 cells (FIGS. 6A and 6B). The transgene expression levels were analyzed over time. While GFP expression was similar between groups (FIG. 11), the MIP.5'OIRP.RHB construct expressed hAAT transgene at about 20-fold higher amounts of transgene protein compared to that obtained using a conventional plasmid pRHB or conventional minicircle MC.RHB 72 hours after transfection, and about 3-fold higher than pMIP.RHB 72 hours after transfection (FIGS. 6A and 6B). These two experiments confirm that the same relative MIP-based enhancement in transgene expression was observed both in vitro and in vivo.

Figure 12A:
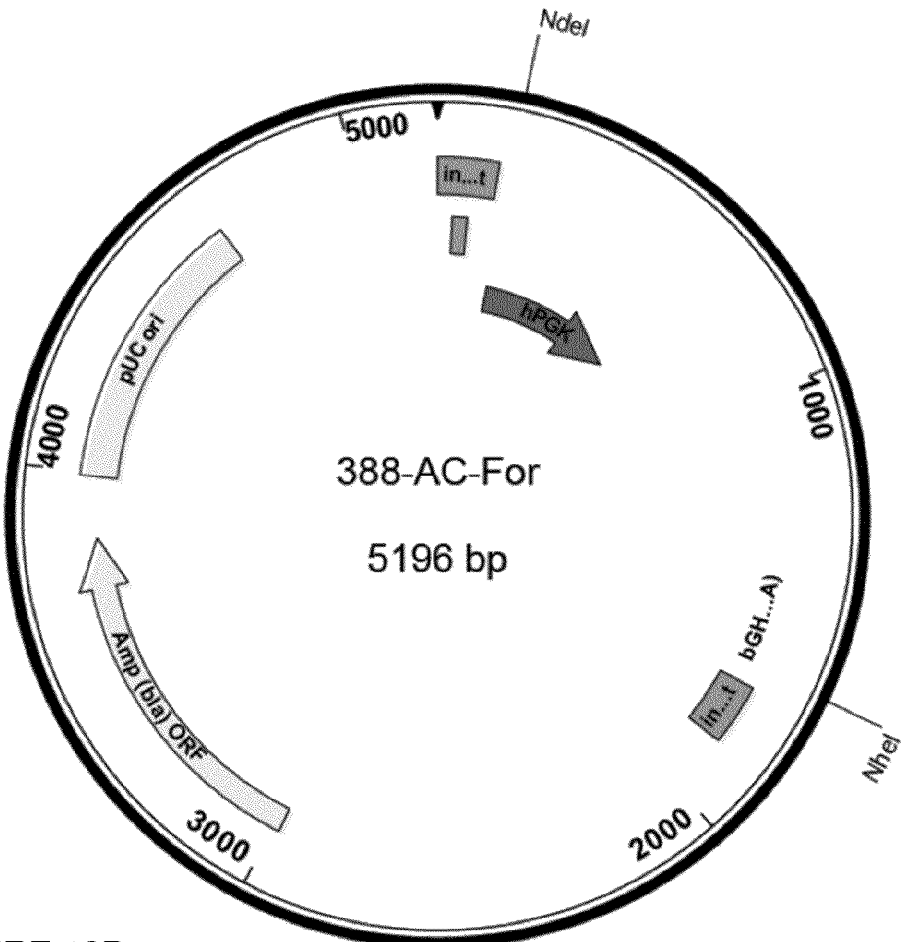
FIG. 12: AAV8-based constructs and transgene expression from a MIP in mice. A) Vector used to produce AAV8. B)
Figure 12B:
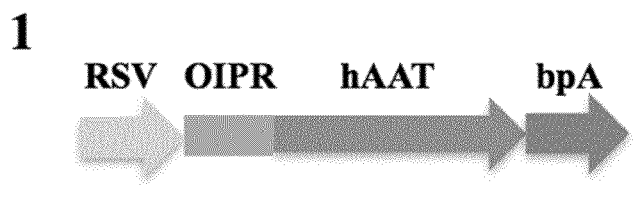
Figure 12B:

The presence of OIPR sequence in the 5' non-coding exon enhances transgene expression from AAV viruses. Adeno-associated virus (AAV) is a non-pathogenic parvovirus that has become one of the most promising viral vectors for use in human gene therapy. AAV8, a serotype discovered in rhesus monkeys, is able to mediate robust transgene expression in various tissues (Gao et al., Novel adeno-associated viruses from rhesus monkeys as vectors for human gene therapy. *Proc Natl Acad Sci USA* 99, 11854-11859, (2002); Nakai et al., Unrestricted hepatocyte transduction with adeno-associated virus serotype 8 vectors in mice. *J Virol* 79, 214-224, (2005); Wang et al., Adeno-associated virus serotype 8 efficiently delivers genes to muscle and heart. *Nat Biotechnol* 23, 321-328, (2005)). By having the OIPR sequence in the 5' non-coding exon, the novel MIP vector persistently expresses transgene product at higher levels than conventional plasmid and minicircle vectors. We wanted to test whether the OIPR sequence can further enhance transgene expression from AAV vectors. Thus the AAV8 recombinant vector genome AAV8.MIP.5'OIPR.RHB was constructed by inserting the RSV-OIPR-hAAT-bpA expression cassette from the MIP.5'OIPR.RHB vector into p388-AC-For by using restriction sites NdeI and NheI (FIGS. 12A and B). As a control, the AAV8 recombinant vector genome AAV8.RHB was constructed by inserting RSV-hAAT-bpA expression cassette into p388-AC-For by using restriction sites NdeI and NheI (FIGS. 12A and B). The final AAV8 viruses were infused into mice. The transgene expression data presented in FIG. 12C showed that the AAV8 containing AAV8.MIP.5'OIPR.RHB recombinant vector genome expressed transgene at ~40 to 50-fold higher than the conventional AAV8 containing AAV8.RHB recombinant vector genome. This confirms that the OIPR sequence, when placed in the 5' non-coding exon of AAV recombinant vector genome, also dramatically enhances transgene expression from AAV virus. This makes the OIPR intron an important factor to enhance transgene expression in both viral and nonviral vectors.

AAV virus production is an expensive and time-consuming procedure. The AAV.MIP dramatically enhances transgene expression. Thus to reach the same transgene expression levels, by using AAV.MIP viruses, only 1/10 to 1/50 of viruses are needed comparing with conventional AAV viruses. This significantly reduces the costs and efforts for virus production.

Discussion

The novel MIP vector system is simple to produce and provides superior expression profiles challenging conventional plasmid and minicircle vector design. The insertion of a PR sequence flanked by optimized splicing sequences into the region before the start codon of transgene, allowed us to achieve transgene expression that was even more robust than that achieved by minicircles both in vivo and in vitro. In this study, we tested three transgenes by comparing conventional plasmid, minicircle and new MIP vectors. For all of the three transgenes, MIP vectors had the highest transgene expression levels. As with minicircle, there was some variation in the relative level of transgene expression using different expression cassettes. This may due to differences in promoter strength, transgene functionality, immune response and sensitivity of analyzing method. However for all tested transgenes, the general patterns were similar with the MIP vector providing the highest level of transgene expression.

The detailed mechanism of enhanced expression over minicircle DNAs and plasmid DNAs is not clear. Our data support the previously reported finding that the RNA-OUT selectable marker in the vector backbone improved transgene expression (Luke et al., Improved antibiotic-free DNA vaccine vectors utilizing a novel RNA based plasmid selection system. *Vaccine* 27, 6454-6459, (2009)). However, since the 5' promoter proximal intron MIP vectors had higher levels of expression in vitro and in vivo transgene expression than standard RNA-OUT plasmids, there are likely additional factors influencing the enhanced expression profiles with the MIP vectors. An intron-mediated transcriptional enhancement has been reported for some plant polyubiquitin genes (Sivamani et al., Expression enhancement of a rice polyubiquitin gene promoter. *Plant molecular biology* 60, 225-239, (2006)) and human ubiquitin C gene (Bianchi et al., A potent enhancer element in the 5'-UTR intron is crucial for transcriptional regulation of the human ubiquitin C gene. *Gene* 448, 88-101, (2009)). It could be possible that the RNA-OUT sequence in the MIP intron functions as a transcriptional enhancer. The inclusion of a spliced promoter proximal intron can enhance transcription levels[18]. Thus the inclusion of the OIPR into a spliced intronic sequence may have had an additive or even synergistic effect on transgene expression.

Recent studies revealed that plasmid DNA silencing in vivo occurs at a nuclear stage that precedes transport of mRNA to the cytoplasm and dramatic enrichment of H3K27 tri-methylation on plasmid sequences was observed compared with minicircle vector (Gracey Maniar, L E et al., Minicircle DNA vector achieve sustained expression reflected by active chromatin and transcriptional level. *Molecular Therapy* (2012, Nov. 27)). These findings indicate that chromatin-linked transcriptional blockage is a possible mechanism of nuclear silencing (Gracey Maniar et al., supra). By keeping the bacterial replication origin and selectable marker in the intron, MIP vector may reduce the incidence of H3K27 tri-methylation on the vector and prevent chromatin-linked transcriptional blockage.

Other types of DNA based gene therapy vectors were developed in recent years, such as pFAR DNA vectors (Marie et al., pFARs, plasmids free of antibiotic resistance markers, display high-level transgene expression in muscle, skin and tumour cells. *The Journal of Gene Medicine* 12, 323-332, (2010)) and NTC vectors (Luke et al., Improved antibiotic-free DNA vaccine vectors utilizing a novel RNA based plasmid selection system. *Vaccine* 27, 6454-6459, (2009)). However, these vectors all have backbone DNA sequences. As previous studied, backbones larger than 1 kb are able to silence transgenes (Lu et al., The extragenic spacer length between the 5' and 3' ends of the transgene expression cassette affects transgene silencing from plasmid based vectors. *Mol Ther* (2012)) with longer backbones having a greater silencing effect. The backbones in pFAR DNA vectors and NTC vectors make them subject to silencing.

Together, the MIP vectors offer an alternative to the popular plasmid and minicircle vector DNAs for promoting gene transfer studies designed to promote biological discovery and therapeutic applications.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts

That which is claimed is:

1. A mini-intronic plasmid (MIP) vector, comprising an expression cassette comprising:
   (a) a promoter operably linked to a transgene,
   (b) an intronic cassette comprising an intron, wherein the intron: (i) comprises a bacterial origin of replication and a selectable marker, (ii) is flanked by a splice donor sequence at its 5' end and a splice acceptor sequence at its 33' end, and (iii) is operably linked to said promoter, and
   (c) a termination sequence,
   wherein the MIP vector comprises less than 1 kb of nucleotide sequence external to the expression cassette and does not comprise a bacterial origin of replication or a selectable marker external to the intron.

2. The MIP vector according to claim 1, wherein the intronic cassette is 5' of the transgene.

3. The MIP vector according to claim 1, wherein the transgene comprises two or more coding exons, and the intronic cassette is flanked by two coding exons.

4. The MIP vector according to claim 1, wherein the intronic cassette is 3' of the transgene and 5' of a termination sequence.

5. The MIP vector according to claim 1, wherein the MIP vector comprises a second expression cassette, wherein the intronic cassette is comprised by the second expression cassette.

6. The MIP vector according to claim 1, wherein the MIP vector is substantially free of bacterial plasmid backbone sequences external to the intronic cassette.

7. The MIP vector according to claim 1, wherein the MIP vector is circular.

8. The MIP vector according to claim 1, wherein the MIP vector is a virus.

9. The MIP vector according to claim 8, wherein the virus is an adenovirus.

10. An isolated nucleic acid, comprising: an intronic cassette comprising an intron, wherein the intron: (i) comprises a bacterial origin of replication and a selectable marker, and (ii) is flanked by a splice donor sequence at its 5' end and a splice acceptor sequence at its 3' end.

11. The nucleic acid according to claim 10, wherein the intronic cassette comprises a 5' exonic splicing enhancer (5' ESE).

12. The nucleic acid according to claim 10, wherein the intronic cassette comprises a 3' exonic splicing enhancer (3' ESE).

13. The nucleic acid according to claim 10, wherein the intronic cassette comprises a G triplet sequence.

14. The nucleic acid according to claim 10, wherein the intronic cassette comprises a polypyrimidine tract.

15. The nucleic acid according to claim 10, wherein the intronic cassette comprises a consensus branch point sequence (BPS).

16. The nucleic acid according to claim 10, further comprising a promoter operably linked to the intronic cassette.

17. The nucleic acid according to claim 10, wherein the nucleic acid is substantially free of bacterial plasmid backbone sequences other than those in the intronic cassette.

18. A method of expressing a transgene in a cell, the method comprising: introducing into a cell a mini-intronic plasmid (MIP) vector comprising an expression cassette comprising:
   (a) a promoter operably linked to the transgene,
   (b) an intronic cassette comprising an intron, wherein the intron: (i) comprises a bacterial origin of replication and a selectable marker, filis flanked by a splice donor sequence at its 5' end and a splice acceptor sequence at its 3' end, and (iii) is operably linked to said promoter, and
   (c) a termination sequence,
   wherein the MIP vector comprises less than 1 kb of nucleotide sequence external to the expression cassette and does not comprise a bacterial origin of replication or a selectable marker external to the intron.

19. The method according to claim 18, wherein the introducing occurs in vitro.

20. The method according to claim 18, wherein the introducing occurs in vivo.

21. The method according to claim 18, wherein the cell is a mammalian cell.

22. The MIP vector according to claim 1, wherein the MIP vector is a plasmid.

23. The method according to claim 18, wherein the MIP vector is a Plasmid.

24. The nucleic acid according to claim 10, wherein said nucleic acid does not comprise a bacterial origin of replication or a selectable marker external to the intron.

25. A mini-intronic plasmid (MIP) vector, comprising an expression cassette comprising:
   (a) a promoter operably linked to a transgene,
   (b) an intronic cassette comprising an intron, wherein the intron: (i) comprises a bacterial origin of replication and a selectable marker, Qpis flanked by a splice donor sequence at its 5' end and a splice acceptor sequence at its 3' end, and (iii) is operably linked to said promoter, and (c) a termination sequence, wherein the MIP vector does not comprise a bacterial origin of replication or a selectable marker external to the intron, and wherein the MIP vector is a plasmid and the plasmid backbone comprises less than 1 kb nucleotide sequence.

26. The MIP vector according to claim 25, wherein the intronic cassette is 5' of the transgene.

27. The method according to claim 18, wherein the MIP vector is circular.

28. The method according to claim 18, wherein the intronic cassette is 5' of the transgene.

29. The method according to claim 18, wherein the MIP vector is substantially free of bacterial plasmid backbone sequences external to the intronic cassette.

30. The MIP vector according to claim 25, wherein the MIP vector is substantially free of bacterial plasmid backbone sequences external to the intronic cassette.

* * * * *